(12) United States Patent
Maher

(10) Patent No.: US 12,419,771 B2
(45) Date of Patent: *Sep. 23, 2025

(54) TEMPERATURE REGULATING PUMP SYSTEM AND ATTACHMENT MECHANISMS THEREOF

(71) Applicant: NeuroRescue, Inc., Westerville, OH (US)

(72) Inventor: Robert Michael Maher, Columbus, OH (US)

(73) Assignee: NeuroRescue, Inc., Westerville, OH (US)

( * ) Notice: Subject to any disclaimer, the term of this patent is extended or adjusted under 35 U.S.C. 154(b) by 223 days.

This patent is subject to a terminal disclaimer.

(21) Appl. No.: 18/232,611

(22) Filed: Aug. 10, 2023

(65) Prior Publication Data

US 2023/0381006 A1 Nov. 30, 2023

Related U.S. Application Data

(63) Continuation-in-part of application No. 17/571,756, filed on Jan. 10, 2022, now Pat. No. 12,011,382, which is a continuation of application No. 16/528,046, filed on Jul. 31, 2019, now Pat. No. 11,219,546, and a continuation of application No.
(Continued)

(51) Int. Cl.
*A61B 5/01* (2006.01)
*A61B 5/00* (2006.01)
*A61F 5/055* (2006.01)
*A61F 7/00* (2006.01)
*A61F 7/02* (2006.01)
*A61F 7/10* (2006.01)

(52) U.S. Cl.
CPC ............ *A61F 5/055* (2013.01); *A61F 7/0085* (2013.01); *A61F 7/10* (2013.01); *A61F 2007/0012* (2013.01); *A61F 2007/0056* (2013.01); *A61F 2007/0095* (2013.01); *A61F 2007/0228* (2013.01); *A61F 2007/0273* (2013.01)

(58) Field of Classification Search
CPC .......... A61F 7/0085; A61F 7/10; A61F 5/055; A61F 2007/0086; A61F 2007/0009; A61F 2007/0056; A61F 2007/0231; A61F 7/106; A61F 2007/0228; A61F 2007/0011; A61B 5/6812; A61B 5/01; A61B 5/4836; A61B 5/6822
USPC ..... 602/14, 5, 1, 2, 18, 41, 60, 61; 607/109, 607/108, 96, 1, 104, 105
See application file for complete search history.

(56) References Cited

U.S. PATENT DOCUMENTS 9,486,354 B2 * 11/2016 Maher .................. A61B 5/6812
10,426,658 B2 * 10/2019 Maher ...................... A61F 7/02
(Continued)

*Primary Examiner* — Tarla R Patel
(74) *Attorney, Agent, or Firm* — McDonald Hopkins LLC

(57) ABSTRACT

A system that selectively controls temperature within a device such as a neck/head wrap is disclosed. The system can include a pump system having a reservoir that holds a liquid, an element that regulates temperature of the liquid within the reservoir; a pump that draws the liquid from the reservoir; and a distribution manifold attached to the pump hose that receives and distributes the liquid to at least two devices (e.g., cervical collars). The system is also equipped to be selectively monitored, for example, via a smartphone, tablet or computer.

13 Claims, 36 Drawing Sheets

Related U.S. Application Data

16/528,090, filed on Jul. 31, 2019, now Pat. No. 11,224,533, said application No. 16/528,046 is a continuation-in-part of application No. 15/287,227, filed on Oct. 6, 2016, now Pat. No. 10,426,658, which is a continuation-in-part of application No. 14/052,346, filed on Oct. 11, 2013, now Pat. No. 9,486,354, which is a continuation-in-part of application No. 13/309,173, filed on Dec. 1, 2011, now abandoned, said application No. 16/528,090 is a continuation-in-part of application No. 15/287,227, filed on Oct. 6, 2016, now Pat. No. 10,426,658.

(60) Provisional application No. 63/396,762, filed on Aug. 10, 2022, provisional application No. 63/523,997, filed on Jun. 29, 2023, provisional application No. 63/525,252, filed on Jul. 6, 2023, provisional application No. 61/419,018, filed on Dec. 2, 2010, provisional application No. 62/834,781, filed on Apr. 16, 2019.

(56) References Cited

U.S. PATENT DOCUMENTS

| | | | |
|---|---|---|---|
| 11,219,546 B2* | 1/2022 | Maher | A61F 7/10 |
| 11,224,533 B2* | 1/2022 | Maher | A61F 5/055 |
| 12,011,382 B2* | 6/2024 | Maher | A61F 7/02 |

* cited by examiner

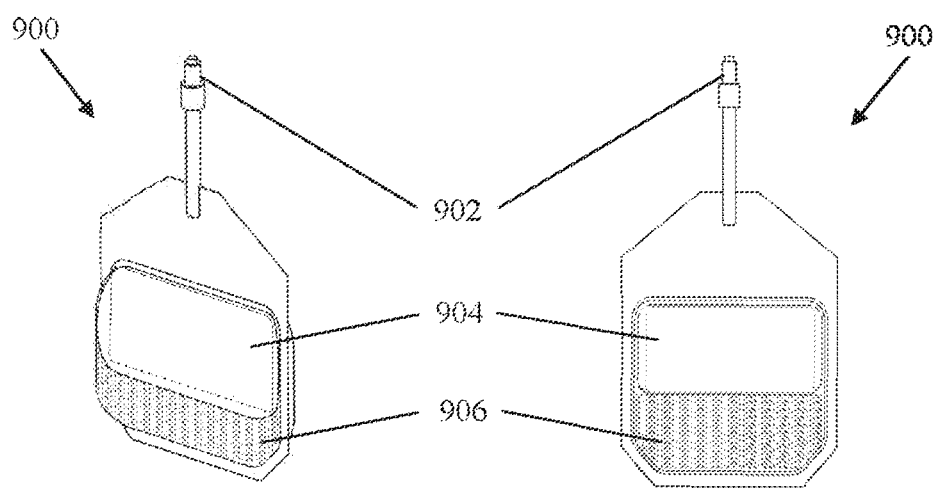
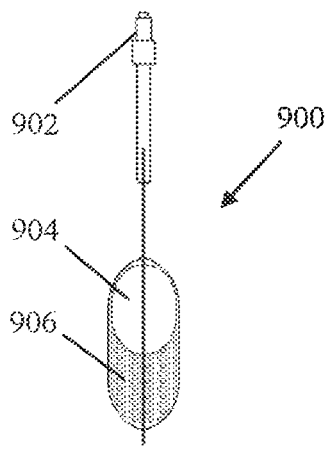
FIG. 9  FIG. 10
FIG. 11

TEMPERATURE REGULATING PUMP SYSTEM AND ATTACHMENT MECHANISMS THEREOF

CROSS-REFERENCE TO RELATED APPLICATIONS

This application is a Continuation-in-Part application and claims the benefit of U.S. Provisional Patent Application Ser. No. 63/396,762 filed Aug. 10, 2022 entitled "COOLING PUMP", and U.S. Provisional Patent Application Ser. No. 63/388,066 entitled "COOLING COLLAR CAP" filed Jul. 11, 2022 and of U.S. Provisional Patent Application Ser. No. 63/523,997 entitled "SYSTEMS FOR TEMPERATURE MANAGEMENT AND BRACKETING SYSTEMS RELATED THERETO" filed Jun. 29, 2023 and U.S. Provisional Patent Application Ser. No. 63/525,252 entitled "COOLING COLLAR CAP" filed Jul. 6, 2023 and is a Continuation-in-Part claiming priority of U.S. patent application Ser. No. 17/571,756 entitled "CERVICAL COLLAR" filed Jan. 10, 2022 which is a continuation of U.S. patent application Ser. No. 16/528,046 entitled "CERVICAL COLLAR" filed Jul. 31, 2019, now U.S. Pat. No. 11,219,546 and a Continuation of U.S. patent application Ser. No. 16/528,090 entitled "CERVICAL COLLAR" filed Jul. 31, 2019, now U.S. Pat. No. 11,224,533 each of which are Continuations-in-Part of U.S. patent application Ser. No. 15/287,227, now U.S. Pat. No. 10,426,658 entitled "CERVICAL COLLAR" filed Oct. 6, 2016, which is a Continuation-in-Part of U.S. patent application Ser. No. 14/052,346, now U.S. Pat. No. 9,486,354, entitled "CERVICAL COLLAR" filed Oct. 11, 2013, which is a Continuation-in-Part of U.S. patent application Ser. No. 13/309,173, now abandoned, entitled "CERVICAL COLLAR" filed Dec. 1, 2011, which claims the benefit of U.S. Provisional Patent Application Ser. No. 61/419,018 entitled "CERVICAL COLLAR" filed on Dec. 2, 2010. Additionally, U.S. patent application Ser. No. 16/528,046 entitled "CERVICAL COLLAR" filed Jul. 31, 2019, now U.S. Pat. No. 11,219,546 and U.S. patent application Ser. No. 16/528,090 entitled "CERVICAL COLLAR" filed Jul. 31, 2019, now U.S. Pat. No. 11,224,533, claim the benefit of U.S. Provisional Patent Application Ser. No. 62/834,781 entitled "CERVICAL COLLAR" filed on Apr. 16, 2019. The entirety of each of the above-noted applications is incorporated herein by reference.

ORIGIN

The innovation disclosed herein relates to a cervical collar and more particularly to a cervical collar employing a cooling device for therapeutic hypothermia.

BACKGROUND

A "neck brace" or "cervical collar" often refers to a medical, and more particularly an orthopedic, device that is often used to support the cervical portion of a patient's spinal cord by immobilizing the head and neck region. These devices are often used by emergency medical technicians (EMTs), for example when responding to victims of traumatic head or neck injuries. Other uses of the devices include treatment of chronic medical conditions, sports injuries or the like.

Traumatic head injury, concussion or neck injury can expose a patient to life altering conditions e.g., extensive spinal cord injury which could escalate to full or partial paralysis, or even death. In an effort to minimize these risks and to stabilize the top vertebrae, EMTs, and other medical personnel, often position a cervical collar on patients as a precautionary measure. Additional stabilization methods can be accomplished by way of other devices such as a backboard. Other uses of the cervical collar are for treatment of injuries including, strains, sprains or whiplash.

The innovation disclosed herein is an improvement to the conventional cervical collars described above.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

In accordance one aspect of the innovation, a system that facilitates therapeutic hypothermia that includes a cervical/neck collar including an outer shell having a front portion and a back portion fixedly coupled to the front portion on one side and removably coupled to the front portion on an opposite side, and a bladder disposed on an interior of the outer shell, wherein the bladder selectively targets blood flowing through cerebral circulation arteries thereby changing a temperature of the blood flowing through the cerebral circulation arteries to a patient's brain.

In accordance with another aspect of the innovation, a system is disclosed that facilitates prevention of over-heating and/or comfort that includes a cervical/neck collar that includes an outer shell having a front portion and a back portion fixedly coupled to the front portion on one side and removably coupled to the front portion on an opposite side, a bladder configured to hold fluid disposed on an interior of the outer shell.

In accordance with another aspect of the innovation, a cervical collar is disclosed that includes an outer shell having a front portion and a back portion fixedly coupled to the front portion on one side and removably coupled to the front portion on an opposite side, a bladder configured to hold fluid disposed on an interior of the outer shell, and an indicator that changes color based on a change in a measurable event, wherein the bladder is the indicator.

In accordance with another aspect of the innovation, a cervical collar is disclosed that includes a bladder without an outer shell. In one aspect, the bladder may comprise an outer portion that is more rigid than an inner portion.

In accordance with still another aspect of the innovation, a method of targeted temperature management (e.g., inducing therapeutic hypothermia or warming) or increasing comfort is disclosed that includes placing a cervical/neck collar on a user's neck (e.g., a patient), circulating cooling or warming fluid through the collar, determining a differential threshold, measuring the patient's core temperature, measuring the patient's cerebral vasculature temperature, determining a difference between the patient's core temperature and the patient's cerebral vasculature temperature, comparing the difference to the differential threshold, and determining if the difference meets the differential threshold. It is to be understood that a patient's skin temperature can be employed in order to obtain all or a subset of comparison temperatures in accordance with the innovation.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIGS. 9-11 are perspective, front and side views respectively of a fluid source in accordance with aspects of the innovation.

DETAILED DESCRIPTION

Figure 1:
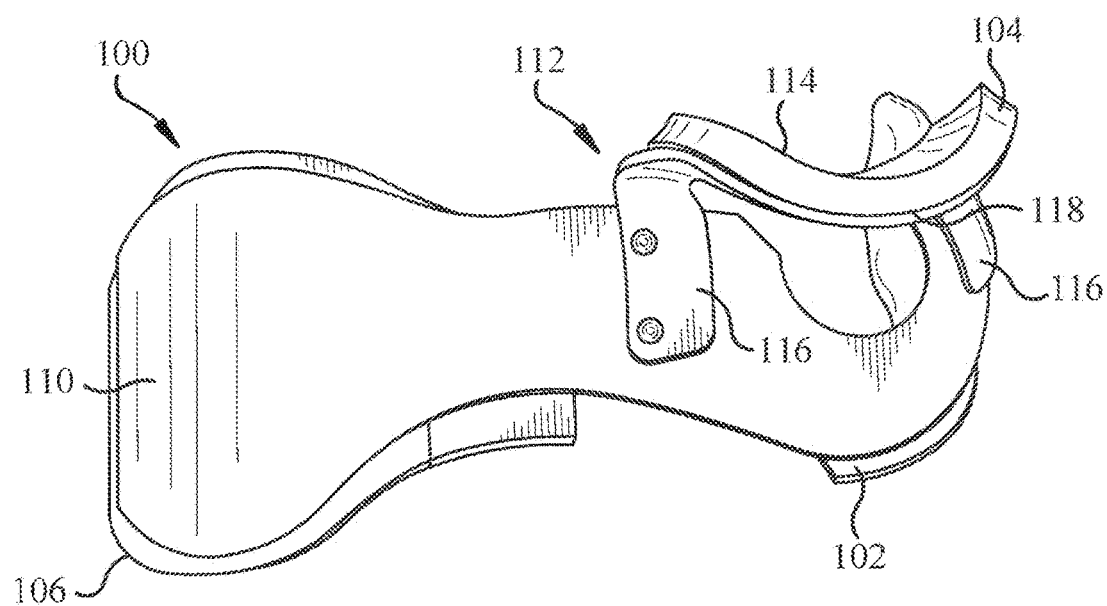
FIGS. 1 and 2 are exterior and interior views of a cervical collar incorporating a cooling device in accordance with aspects of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. Moreover, not all illustrated acts may be required to implement a methodology in accordance with the innovation.

Following is a discussion of the innovation and some example applications of the features, functions and benefits of employing a stabilizing device having a cooling (or warming device for certain medical (and therapeutic) applications) device as described herein, for example, following traumatic head injury, concussion or neck injury. The innovation, in a broad application, is directed to the concept of induced or therapeutic hypothermia. Therapeutic hypothermia is a medical treatment for lowering one's core temperature to, for example, around 33° Celsius or other target temperature. Therapeutic hypothermia can be used to reduce the risk of tissue injury due to a period of insufficient blood flow caused by, for example, cardiac arrest or the occlusion of an artery by an embolism, as often occurs in the case of strokes. Studies have demonstrated, as is appreciated by those knowledgeable in the art that patients at risk for ischemic brain injuries have better results if treated with therapeutic hypothermia within the first sixty minutes, known as the "golden hour" by medical personnel, after the traumatic event.

Therapeutic hypothermia may be induced by either invasive or non-invasive procedures. Some non-invasive procedures may include packing or placing cold packs, cold compresses in the axil area, under the armpits or in the groin area to try to cool blood vessels. Another non-invasive procedure includes placing a chilled water blanket or torso vest and/or leg wraps in direct contact with the patient's skin. Some invasive procedures may include administering approximately 2,000 ccs (two bags) of a normal chilled saline solution, often referred to as a crystalloid, or placing a catheter in the inferior vena cava via the femoral vein.

The innovation disclosed herein enables pre-hospital care providers to get a thorough jumpstart of inducing therapeutic hypothermia through a non-invasive procedure. As used herein, pre-hospital care providers can include care administered by EMTs, paramedics, army medics, sports trainers, etc. In other words, the innovation can be employed by most anyone in the field. Similarly, the features, functions and benefits can be employed in a hospital or other medical care facility without departing from the spirit and/or scope of the innovation described herein. Thus, the innovation disclosed herein can be used by any type of medical personnel including those in the field or in a facility by a medical professional or caregiver.

While the innovation and the example embodiments described herein are directed to a cervical collar that includes a cooling device to target the carotid artery, it is to be appreciated that the features, functions and benefits of the innovation can be applied to other regions of the body for cooling or warming and for uses other than medical or therapeutic uses. Essentially, most any region whereby blood flows and can be affected by the cooling device of the cervical collar. In one embodiment, the cervical collar may act as a stabilizing device. For instance, areas where pulse points are located are most often good candidate regions for placement of the innovation. For example, in addition to the spinal/neck region, the innovation can be employed in the axil area, groin area, legs, arms, torso, etc. As will be understood, in order to enhance effects of cooling, it is important to cool as much blood as possible, thus, highly vascular regions are key regions for implementation, e.g., jugular veins, carotid arteries. In addition, it is to be understood that the innovation disclosed herein can also be used as a warming device. Thus, the innovation can be connected to a fluid source that can be used to circulate warming fluid through the innovation as described herein. Therefore, the example cervical collar disclosed herein is for illustrative purposes only and is not intended to limit the scope of the innovation.

In accordance with some aspects of the innovation, the innovation facilitates the placement of the cooling device in strategic anatomical positions on the neck region. Thus, the cooling device of the cervical collar can target the carotid arteries, which supplies the supply of blood flow to the brain, in the interior portion of the neck. In other aspects, the cooling device can target the posterior portion of the neck to cool the cervical areas of the neck to decrease swelling around the posterior portion of the neck including the spinal cord area and essentially cooling the neck as a whole. Thus, the cervical collar is capable of decreasing the temperature of the blood in highly vascular regions so as to enhance induced hypothermic reaction. More specifically, the cervical collar can selectively cool the cerebral vasculature relative to the whole body thereby inducing hypothermia. Because the cooling effect to the patient is targeted to a specific area (e.g., the brain), any side effects associated with whole body cooling are significantly reduced. Effectively, the cervical collar can most often be employed in three primary scenarios, stroke, heart attack, and head/neck injury or trauma.

It is to be understood that the innovation may be employed in non-medical and non-therapeutic scenarios. Reference to a "patient" is intended to include any user.

It is also to be understood that reference to a "cervical collar" is intended to include any device that can be worn around the neck to offer cooling/heating as described herein. It is intended that the terms "cervical collar," "cervical/neck collar" and "collar" be used interchangeably.

For example, the cervical/neck collar may be used to provide comfort or to prevent over-heating (e.g., heatstroke in, for example, a hot environment or during strenuous activities that include heavy equipment, such as military exercises/operations or athletics). It is further contemplated that a user may utilize the collar in situations where cooling would provide comfort. For example, the user may be outside on a hot day and may utilize the collar for purposes of comfort. It is also contemplated that the cervical collar could be used to prevent over-heating in situations where over-heating is suspected or possible. For example, during athletic events, a user may become over-heated or be in danger of becoming over-heated. In another example, the collar could be used by a first responder or soldier in situations involving extreme temperatures (hot or cold). The cervical collar could be employed prophylactically before signs of over-heating appear or could be employed once signs of over-heating appear so as to provide comfort and reduce the risks associated with over-heating.

It is also to be appreciated that any of the methods described herein are applicable to any user, whether for medical or non-medical purposes.

Figure 2:
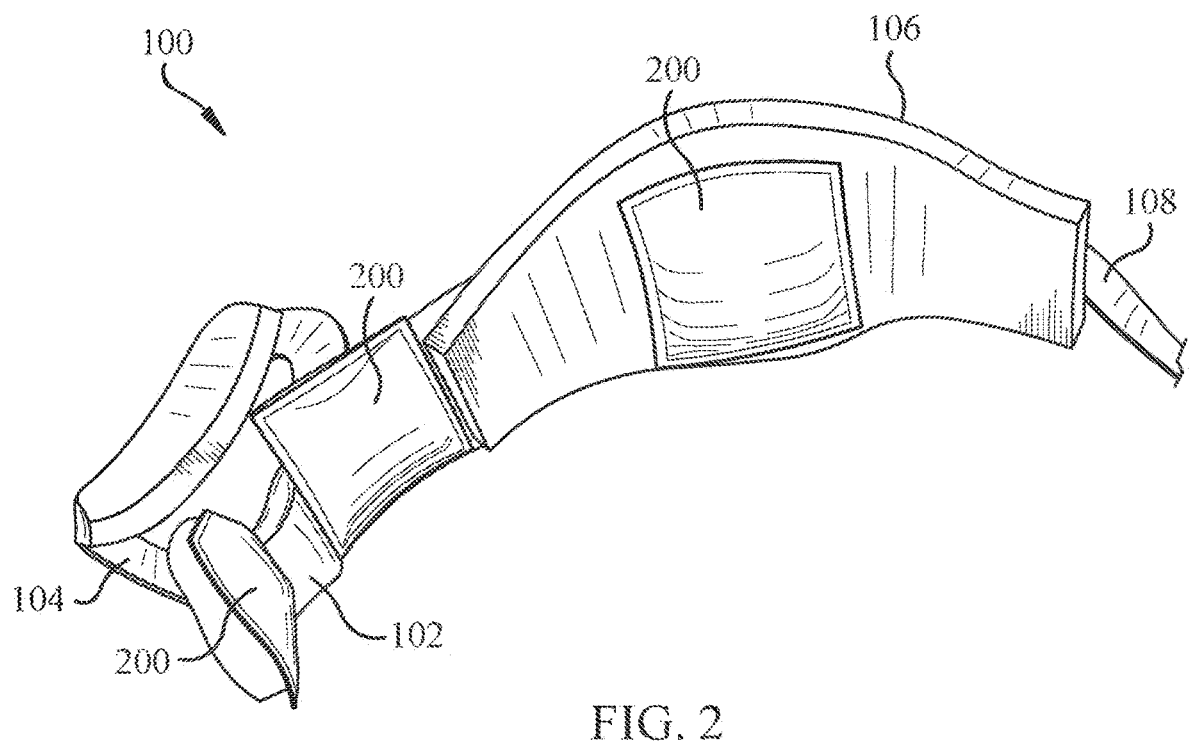

Referring now to the figures, FIGS. 1 and 2 illustrate an example embodiment of a stabilizing device, such as a cervical collar 100 that includes a cooling device in accordance with aspects of the innovation. The cervical collar 100 is most often used to immobilize one's neck in a trauma situation. The cervical collar 100 includes a front portion 102, an optional support 104 for supporting a patient's chin attached to the front portion 102, a back portion 106, and a fastening device 108 such as a strap. The fastening device 108 is attached to one side of the back portion 106 and extends toward the front portion 102. When the patient is wearing the cervical collar 100, the fastening device 108 removably attaches one side of the front portion 102 to thereby couple the front portion 102 to the back portion 106. The fastening device 108 may be any type of device, such as but not limited to a strap that employs a Velcro™-type fastener, snaps, buttons, hooks, etc. For example, additional embodiments can be equipped with a dongle, tag or other suitable mechanism on the strap that can enhance usefulness and increase dexterity in adjustment, i.e., loosening and/or tightening the strap. It is to be appreciated that most any means for attachment and/or adjustment can be employed in accordance with other aspects of the innovation. It is to be further appreciated that the fastening device 108 is adjustable to allow the cervical collar 100 to conform to patients having different sized necks. It is to be appreciated that in some embodiments, the collar does not fully encircle a user's neck. In some embodiments, the collar may include a contiguous portion that is configured to securely fit around a user's neck without coupling a front portion and a back portion to encircle the user's neck. In some embodiments, the collar may have a generally U-shaped configuration. In other embodiments, the collar may be equipped with magnets on the surface of or between the layers of materials making up the composition of the collar. It is to be understood and appreciated that the magnets could be utilized for means of attaching the collar to a surface, e.g., the back of a bench or to any surface of the pump (e.g., the pump referenced below) such that the collar is contained and not falling on the ground when not in use. In addition to magnets, other means of attachment are contemplated and to be included within the spirit and/or scope of this specification. By way of example, but not limitation, the collar can be equipped with snaps, Velcro, grommets (that mate to hooks), etc.—all of which are to be included within the spirit and scope of the innovation herein. Moreover, it is to be understood and appreciated that embodiments can include collars having an ability to host weights on or within the layers of material.

The front and back portion 102, 106 are both made from a soft foam material that can be bent to conform to with the patient's neck, back, and shoulders. It is to be appreciated, however, that the front and back portion 102, 106 can be made from any suitable material as long as it conforms to the patient's neck, such as but not limited to, natural and synthetic polymers, carbon-reinforced materials, metal wire reinforced materials, etc.

It is to be appreciated that, while immobilization in specific scenarios (e.g., neck immobilization) is discussed in detail, the innovation and its features, functions and benefits can be used in other applications and scenarios without departing from the spirit and scope of the cooling effects described herein. In other words, it is to be understood that, while enhancing the cooling effects in response to an injury or condition, in accordance with some embodiments of the innovation need not also immobilize an injured area (e.g., the spinal area). These additional embodiments are to be included within the scope of the disclosure and claims appended hereto.

Referring specifically to FIG. 1, a flexible integrated outer shell 110 is attached to both the back portion 106 and the front portion 102 thereby coupling the other side of the front portion 102 to the other side of the back portion 106. The outer shell 110 can be attached to the front and back portion 102, 106 via any suitable means, such as but not limited to, an adhesive, rivets, etc. The outer shell 110 is flexible in a horizontal direction thus, allowing the cervical collar 100 to attach around the patient's neck. The outer shell 110, however, is more rigid in the vertical direction thus, giving the cervical collar its stabilization characteristics. In one embodiment, the outer shell may be flexible (e.g., not rigid in any direction) for circumstances where immobilization is not desired/warranted. The outer shell 110 can be any suitable rigid material or non-rigid material, such as but not limited to a molded plastic (e.g., polyethylene, polystyrene, etc.).

It is to be appreciated that, while a cervical collar having an outer shell is discussed in detail, the innovation includes embodiments wherein the cervical collar does not include a separate outer shell. In other words, the cervical collar may include a bladder (described more fully below) and does not include a separate outer shell. These embodiments are to be included within the scope of the disclosure and the claims as appended hereto.

Still referring to FIG. 1, the support 104 for supporting the patient's chin, also referred to as a chin cup, is attached to the front portion 102. It is to be appreciated that the support 104 is an optional device and the cervical collar 100 can still perform its intended function in accordance with aspects of the innovation without employing the support 104. The support 104 is disposed beneath the patient's chin for cervical support. The support 104 includes an attachment piece 112 that attaches to the front portion 102 and a rest piece 114. The attachment piece 112 includes two leg members 116 and a curved portion 118 connecting the two leg members 116. The leg members 116 are attached, via rivets or any other suitable means, to the front portion 102 to secure the support 104 to the cervical collar 100. The rest piece 114 is attached, via an adhesive or any other suitable means, to the curved portion 118 to support the patient's chin.

The support 104 can be fixedly attached or adjustably attached to the cervical collar 100. It is understood that individuals have different size necks and chins. Thus, in accordance with aspects of the innovation, the support 104 can be height (or otherwise) adjustable or interchangeable to facilitate comfort and enhanced immobilization effect. For example, in accordance with aspects of the innovation, the support 104 can be adjusted using a tongue and groove mechanism, where the support 104 can act like a tongue and the cervical collar 100 can employ the associated grooves. In accordance with other aspects of the innovation, the support 104 can include preselected heights. For example, a spring-button can be used that catches within a hole in the cervical collar 100 to secure the support 104 at a pre-selected height position. It is to be appreciated that other aspects can employ grooves, hardware (e.g., wing-nuts), etc. for adjustment without departing from the scope of the innovation. Thus, the adjustability of the support 104 and the cervical collar 100, via the fastening device 108, provides a universal fit and applicability of the innovation. Therefore, the cervical collar 100 is adjustable for both length (e.g., support 104) as well as width (e.g., fastening device 108).

In the examples illustrated below, the cervical collar 100 further includes a cooling device that may be in the form of a cooling pack (e.g., chemical pack) integrated into the cervical collar 100, a retainer to receive and hold a cooling pack (e.g., chemical pack, ice pack, sterile water cooling pack, etc.), or a bladder having chambers to allow cooling fluid to be pumped through essential portions of the cervical collar 100. It is to be appreciated that while pumping cooling fluid through the chambers of the bladder is described specifically herein, any method/means of causing cooling fluid to circulate throughout the bladder can be used without departing from the spirit and scope of the circulation of cooling fluid described herein. In other words, cooling fluid may be pushed and/or pulled to accomplish the desired circulation of cooling fluid. In specific examples, a pump or other circulation device can be disposed within the collar(s) to effect the pump or draw of liquid in accordance temperature management (cooling or heating). These alternative aspects are to be included within the spirit and scope of this disclosure and claims appended hereto. Furthermore, while many aspects discuss "cooling," it is to be appreciated that this term is to relate to temperature management generally thereby including warming/heating as well.

While the embodiments described herein are generally related to fluids in a liquid state, it is to be appreciated that alternative aspects exist that employ other fluid states/phases such as air and gas to accomplish the features, functions and benefits described herein. These alternative embodiments are to be included within the scope of this specification and claims appended hereto.

The cervical collar 100 may optionally include features to permit access to areas of a patient for administration of medications or other treatments. For example, the cervical collar may include medical application openings within the outer shell. These openings may be strategically placed so as to permit access to specific regions (e.g., veins). In one embodiment, these openings may comprise perforated or otherwise removable portions to permit customized access according to need. For example, the medical application opening may comprise a portion of the cervical collar (e.g., the outer shell or the bladder if there is no outer shell) that is removable with force (e.g., pressure applied to a perforated region) to create medical application opening(s) only where needed.

In an alternate embodiment, at least a portion of the cervical collar (e.g., the outer shell or the bladder if there is no outer shell) comprises a penetrable material (e.g., able to be penetrated by medical equip such as a needle).

In yet another alternate embodiment, at least a portion of the cervical collar may include a movable portion to permit access. For example, the material may be arranged in overlapping slats wherein each slat is at least somewhat moveable so as to permit access for medical treatment (e.g., insertion of a needle for medication or an IV).

FIG. 2 illustrates one example embodiment of the cooling device in accordance with aspects of the innovation. The cooling device in this embodiment is a cooling pack 200 that can be either integrated into the cervical collar 100 or can be inserted into a retaining device described below. The cooling pack 200 can be strategically disposed at essential locations on the cervical collar 100 to target the areas of the neck described above. For example, one or more cooling packs 200 can be located on the front portion 102 to target the carotid arteries. In addition, one or more cooling packs 200 can be located on the back portion 106 to target the spinal cord area. The cooling pack 200 can be any type of cooling pack, such as but not limited to chemical pack (e.g., granule-activation packets that when activated releases a cooling agent to provide the desired cooling effect). For example, the granule-activation packets use ammonium nitrate and water. When a user strikes the cooling pack 200 with the palm of a hand, a prescribed amount of water will mix with the ammonium nitrate thereby creating a cold compress. Once the cooling packs 200 are activated, the cervical collar 100 can be placed on the patient to provide the desired therapeutic hypothermia to essential portions of the neck area described above.

The retaining device receives and holds a cooling pack, such as but not limited to, an ice pack or a chemical pack as described above. The retaining device can be strategically disposed at essentials locations on the cervical collar 100 to target the areas of the neck described above. For example, one or more retaining devices can be located on an interior side of the front portion 102 to target the carotid arteries. In addition, one or more retainers can be located on an interior side of the back portion 106 to target the spinal cord area. The retaining device can be in the form of a pocket, a pouch, straps, etc. and can be made from any suitable material, such as but not limited to, plastic, a mesh like material, etc. that sufficiently conducts the cooling effects of the cooling pack. It is to be appreciated that the options for the type and material of the retaining device are limitless and as such all of which are included in the scope of the innovation.

Figure 3:
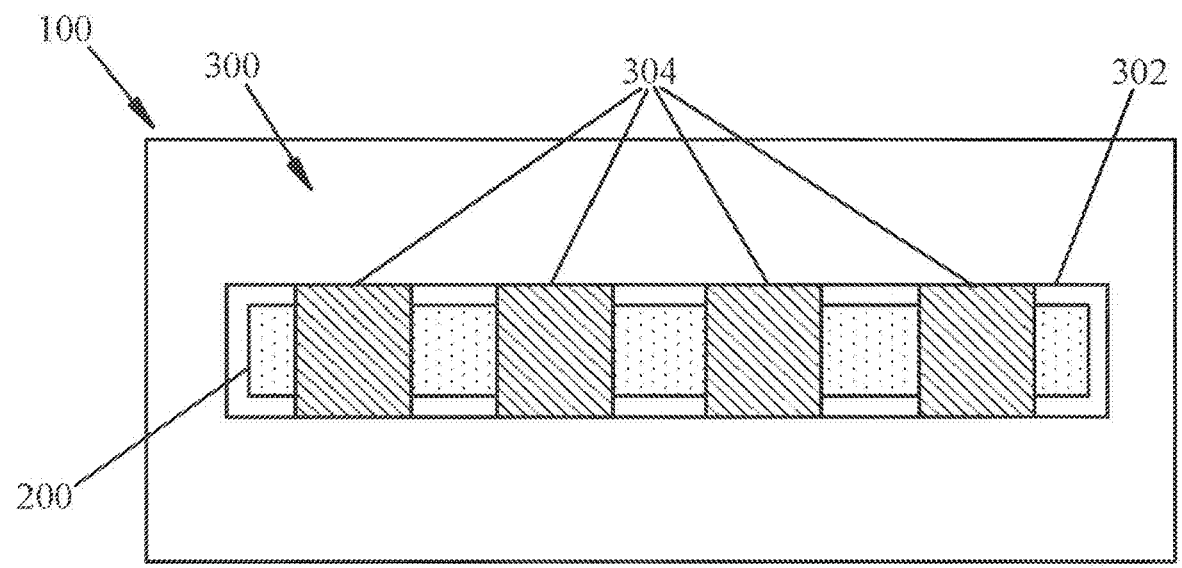
FIG. 3 is a block type diagram of the cervical collar of FIGS. 1 and 2 incorporating an example embodiment of the cooling device in accordance with aspects of the innovation.

For example, FIG. 3 is a block diagram illustration of the cervical collar 100 described above incorporating an example retaining device 300 in accordance with aspects of the innovation. The retaining device 300 includes a channel 302 and one or more covers 304 to hold the cooling pack 200 described above in place. The cover 304 may be made from any material that sufficiently conducts the cooling effects of the cooling pack 200 and that does not irritate the patient's skin. Further, the cover 304 can be a single piece or multiple pieces. In this embodiment, the cervical collar 100 can be packaged and transported in a flat condition to save space in transport vehicles such as emergency medical vehicles. When emergency personnel require the use of the cervical collar 100, the cooling pack 200 can be inserted or slid into the channel 302 and placed on the patient. When the cervical collar 100 is placed on the patient, the cooling pack 200 will activate thereby providing the required cooling effect. It is to be appreciated that the cooling pack 200 can be integrated into the channel 302 thus, saving the emergency personnel the time of placing the cooling pack into the channel 302. Once the cooling packs are secured by the one or more retaining devices, the cervical collar 100 can be placed on the patient to provide the desired therapeutic hypothermia to essential portions of the neck area described above.

Figure 4:
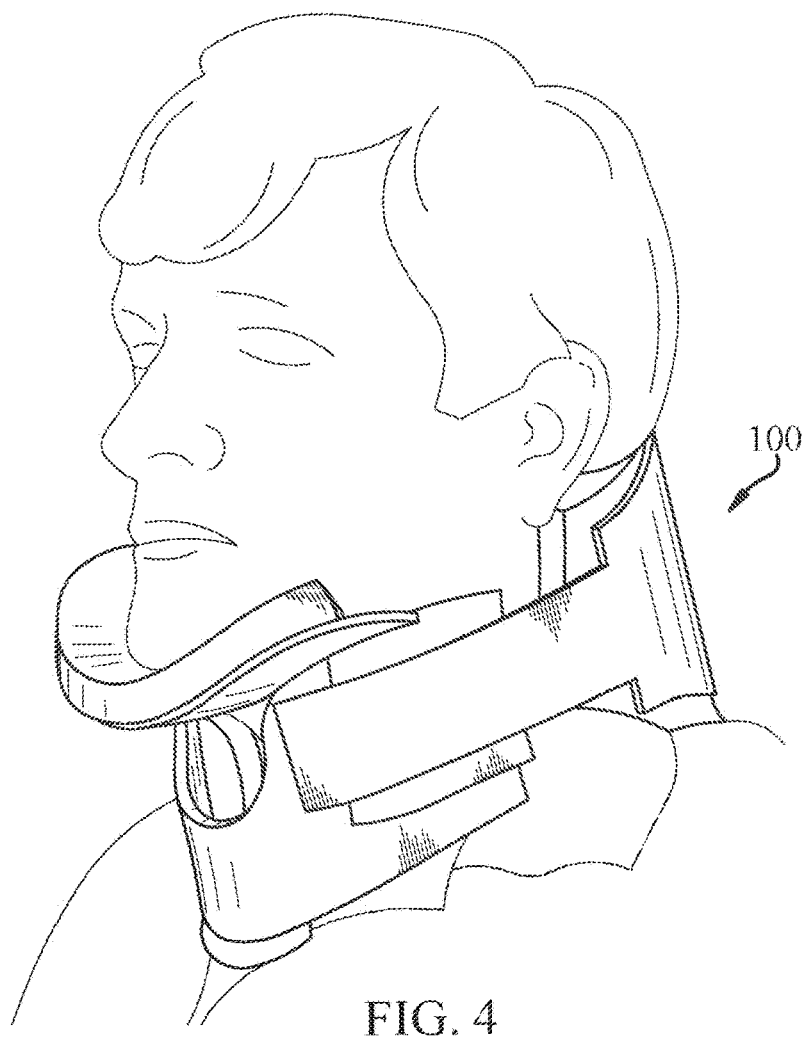
FIG. 4 is a perspective view showing the cervical collar of FIGS. 1 and 2 fitted to the patient in accordance with aspects of the innovation.

For example, FIG. 4 illustrates a perspective view of the cervical collar 100 described above fitted on a patient. As illustrated, the cervical collar 100 has the ability to provide therapeutic hypothermia upon vascular regions to facilitate promptly treating a patient and to minimize risk of further injury than that of conventional cervical collars.

FIGS. 5-8 represent another example embodiment of a cervical collar 500 (hereinafter "collar") incorporating a cooling/warming device. In this embodiment, the cooling/warming device allows cooling (or warming) fluid from an external fluid source, such as but not limited to, a portable fluid source or an external continuous fluid system to be squeezed or pumped into and/or circulated through essential portions of the collar 500. The collar 500 includes an outer shell 502, an adjustable support (not shown), and a bladder 506. It is to be appreciated that while the collar 500 can be used for inducing hypothermia, in some embodiments, the collar 500 can also be used for other purposes when a patient does not require therapeutic hypothermia. In one embodiment, the collar may be in fluid communication with additional cooling/warming devices such as a vest having a cooling/warming bladder or cooling/warming pouch. The vest may also be connected to a portable fluid source or an external continuous fluid system that is the same or different than the fluid source for the collar.

Figure 6:
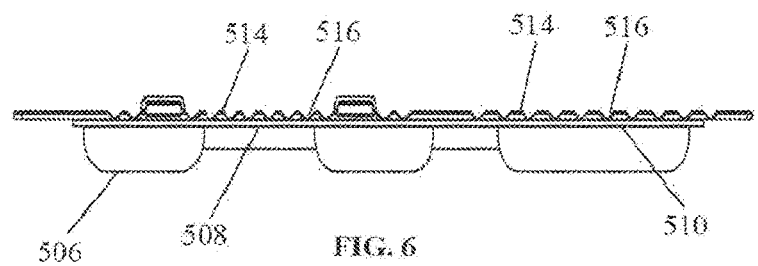
FIG. 6 is a top view of the cervical collar of FIG. 5 in accordance with aspects of the innovation.
Figure 7:
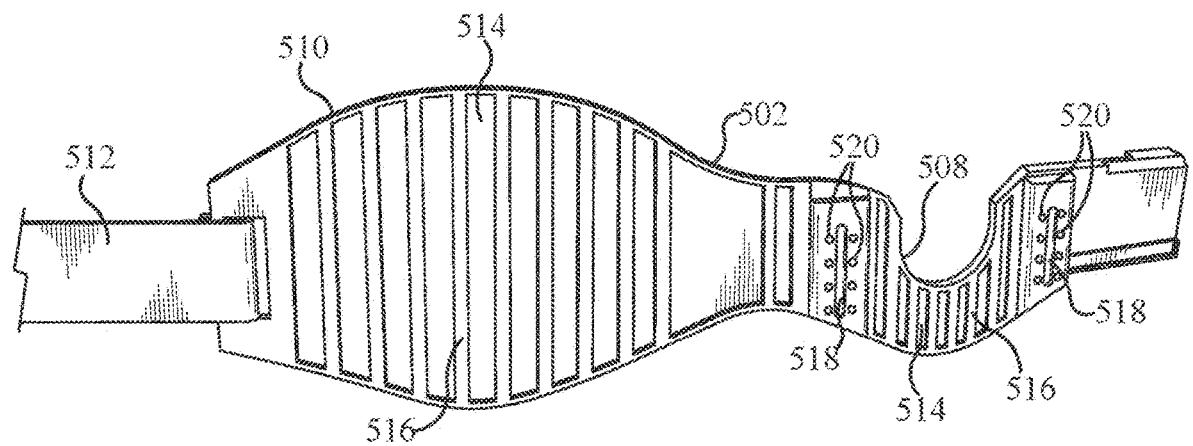
FIG. 7 is a rear view of the cervical collar of FIG. 5 in accordance with aspects of the innovation.

Referring to FIGS. 6 and 7, the outer shell 502 includes a front portion 508 fixedly coupled to a back portion 510 on one side and a fastening device 512 attached to the back portion 510 and removably coupling the front and back portions 508, 510 on an opposite side. The features of the fastening device 512 are similar to the fastening device 108 described above and, as such, will not be repeated.

The outer shell 502 is made from a flexible plastic material, such as but not limited to polyethylene, polystyrene, etc. Further, both the front and back portions 508, 510 include multiple panels 514 each connected by hinged portions 516 that further facilitate in the flexibility of the outer shell 502. This configuration allows EMT personnel to control the flexibility of the collar 500 and easily adjust the collar 500 to fit the patient. In addition, the flexibility characteristic allows the collar 500 to be packaged in a flat state thereby optimizing volume space for shipping and/or storage purposes. The front portion 508 of the outer shell 502 further includes multiple slots 518 and multiple recesses 520 disposed on each side of each slot 518. The multiple slots 518 and multiple recesses 520 facilitate attachment and adjustment of the support to the collar 500 subsequently described.

The support is used to support the patient's chin and is adjustable to conform to the patient similar to the support 104 described above. The support includes attachment legs that attach the support to the front portion 508 and a connection part connecting distal ends of the attachment legs. The connection part serves to support the patient's chin. Multiple slots 518 are defined in the front portion 508 to receive the attachment legs to thereby connect the support to the collar 500. The support can be adjusted by sliding each attachment leg in each slot 518 to a desired position. The attachment legs engage recesses 520 defined on each side of each slot 518 to lock the support in its desired position.

As mentioned above, the connection part provides a connection between the distal ends of the attachment legs. The connection point between the attachment legs and the connection part is hinged to facilitate packaging. Specifically, when the collar 500 is packaged in a flat state, mentioned above, one attachment leg is disconnected from the collar 500 and laid in a flat state. This is possible because of the hinged connection.

Figure 8:
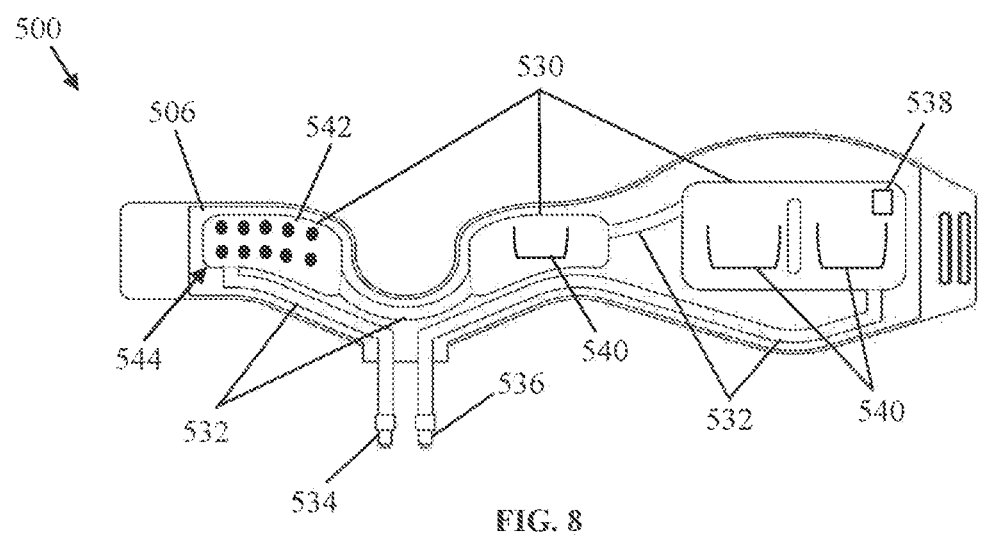
FIG. 8 is a front view of the cervical collar of FIG. 5 in accordance with aspects of the innovation.

Referring to FIG. 8, the bladder 506 is a single piece bladder type device that includes multiple cooling chambers (or reservoirs) 530, multiple passageways 532, an inlet port 534, and an outlet port 536. The passageways 532 provide a fluid connection between the chambers 530 and the inlet port 534, between the chambers 530 and the outlet port 536, and between the chambers 530 themselves.

The bladder 506 attaches to an interior portion of the outer shell 502 and can be made from multiple sheets of a flexible material that is conducive to conducting the cooling effects of the cooling, such as but not limited to, polyethylene. The multiple sheets can be arranged in numerous configurations, such as but not limited to, two sheets, three sheets, four sheets, etc. In instances where there are more than two sheets, multiple layers may be arranged on the patient side of the bladder 506 to facilitate the prevention of frost bite. The bladder 506 may be attached to the interior portion of the outer shell 502 by any suitable means, such as but not limited an adhesive.

As described above, in one embodiment, the cervical collar may not include a separate outer shell. The bladder may include a back portion (e.g., a patient side) and front portion. In one embodiment, the front portion of the bladder may comprise a more rigid material than the patient side. In one embodiment, the back portion may fixedly coupled to the front portion on one side and removably coupled to the front portion on an opposite side.

The chambers 530 are an integral part of the bladder 506. Specifically, to form the chambers 530, the two flexible sheets are placed in a heat mold and hermetically sealed in an area surrounding the desired location of each chamber 530. Although, the number of cooling chambers 530 illustrated in FIG. 8 is three, it is to be understood that the innovation is not dependent on the number of chambers 530 formed in the bladder 506. Thus, the example embodiment described herein and illustrated in the figures is for illustrative purposes only and is not intended to limit the scope of the innovation. It is to be appreciated, however, that the number and location of the chambers 530 targets essential areas of the patient's neck (e.g., carotid arteries, spinal area, etc.) to provide optimum cooling to the cerebral vasculature.

For example, the innovative cervical collar 500 may be configured to selectively cool or target cerebral circulation arteries, which are arteries that supply blood to the brain. More specifically, the cervical collar 500 may be configured to target arteries that supply blood to the anterior portion of the brain, known as anterior cerebral circulation. These arteries include the internal (intracranial) carotid arteries, external carotid arteries, anterior cerebellar arteries, anterior inferior cerebellar arteries, middle cerebral arteries, anterior spinal arteries, the anterior communicating arteries, and the ophthalmic arteries. The cervical collar 500 may also be configured to target arteries that supply blood to the posterior portion of the brain known as posterior cerebral circulation, including the occipital lobes, the cerebellum, and the brainstem. These arteries include vertebral veins and arteries including subclavian arteries, basilar arteries, posterior cerebral arteries, posterior cerebellar arteries, posterior inferior cerebellar arteries, posterior communicating arteries, pontine arteries, the superior cerebellar arteries, and the posterior spinal artery. In addition, the innovative cervical collar can also be configured to provide cooling to portions of the cranium, such as but not limited to the petrous bone.

As mentioned above, the passageways 532 provide a connection between the chambers 530, and between the chambers 530 and the inlet and outlet ports 534, 536. The passageways 532 may be comprised of embedded tubes or may be integrally formed in the bladder 506. Specifically, multiple tubes can be positioned at proper locations in the bladder 506 during formation of the chambers 530 described above, thus, embedding the tubes in the bladder 506. The passageways 532 may also be integrally formed in the bladder 506 by hermetically sealing an area surrounding each passageway 532 similar to the formation of the chambers 530 described above.

The inlet and outlet ports 534, 536 provide a connection between the bladder 506 and the external fluid system or source. The connection between the bladder 506 and the external fluid system or source can be any suitable mechanical connection device, such as but not limited to, quick couplers, a screw type device, etc. Further, the inlet and outlet ports 534, 536 may include a valve to regulate the flow of cooling fluid into and/or out of the bladder 506. It is to be appreciated that the inlet port 534 and the outlet port 536 can be switched. In other words, the inlet port 534 can serve as the outlet port 536 and the outlet port 536 can serve as the inlet port 534.

In one embodiment, the bladder may include multiple inlet and outlet ports configured to provide multiple connections between the bladder and a temperature modulation source (e.g., cooling or warming fluid).

Alternatively, still referring to FIG. 8, pockets or sleeves 540 may be attached to one or more chambers 530 that accept cooling packs 200 described above. The cooling packs 200 may be used in the event that the external fluid system of source is not available.

In still yet another embodiment shown in FIG. 8, one or more of the chambers 530 may include internal fasteners that connect a front 542 of the chamber to the back to thereby create a dimpled pattern 544. The dimpled pattern 544 flattens out the front surface 540 of the chamber 530 to allow more surface area to contact the patient. In addition, the internal fasteners cause the fluid inside the chambers 530 to flow in more a random pattern.

Figure 8A:
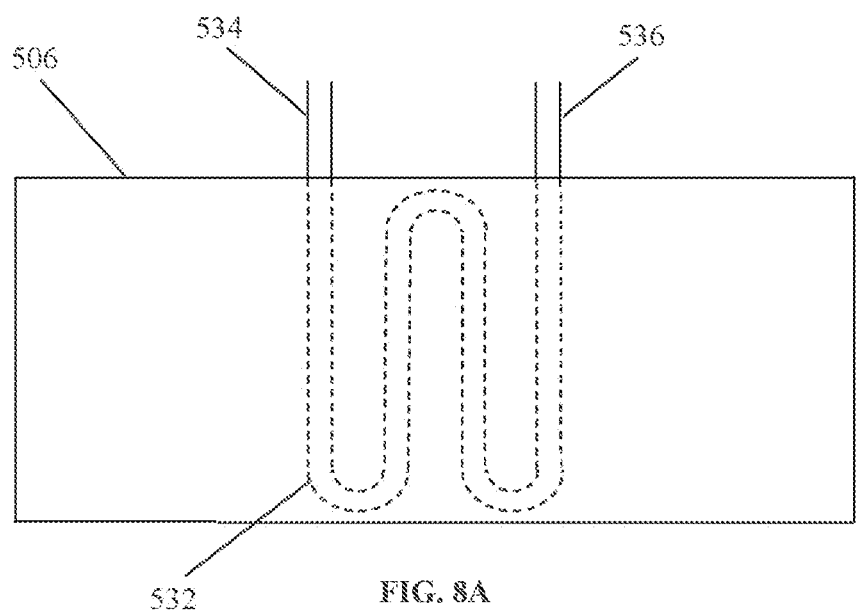
FIG. 8A is a block type diagram of another embodiment of a cervical collar incorporating a cooling device in accordance with aspects of the innovation.

In an alternative embodiment shown in FIG. 8A, the bladder 506 can be modified to exclude the chambers and simply include passageways 532 that run through the bladder 506 in desired locations. The passageways 532 would connect to both the inlet and outlet ports 534, 536 to allow the continuous circulation of cooling fluid, as described above.

One such example of a fluid source is a portable cooling pack 900 illustrated in FIGS. 9-11. The portable cooling pack 900 includes a port 902 that acts as both an inlet port and an outlet port. The portable cooling pack 900 is a granule-activation packet that uses a fluid 904, such as but not limited to, water and a chemical 906, such as but not limited to, ammonium nitrate that when mixed together create a cooling fluid. When a user strikes the portable cooling pack 900 with the palm of their hand, a prescribed amount of water will mix with the ammonium nitrate thereby creating a cooling fluid. The cooling fluid from the portable cooling pack 900 can then be mechanically pumped or hand squeezed into the bladder 506 via the inlet port 534 and into each chamber 530 via the passageways 532, as described below.

In addition, once the cooling fluid inside the bladder 506 begins to warm, the empty cooling pack 900 can be attached to the outlet port 536 and a new portable cooling pack 900 can be attached to the inlet port 534. The cooling fluid from the new portable cooling pack 900 can then be pumped or squeezed into the bladder 506 thereby forcing or flushing the warm fluid out of the bladder 506 through the outlet port 536 and back into the original cooling pack 900. Thus, cooling fluid can essentially be continuously pumped through the collar 506 by EMT personnel who do not have access to a continuous external cooling system (described below) in the field. In addition, the fluid may be manually squeezed (or pumped) out of the bladder 506 such that the cervical collar 500 can function as a collar without the need to pump fluid through the bladder 506.

Figure 11A:
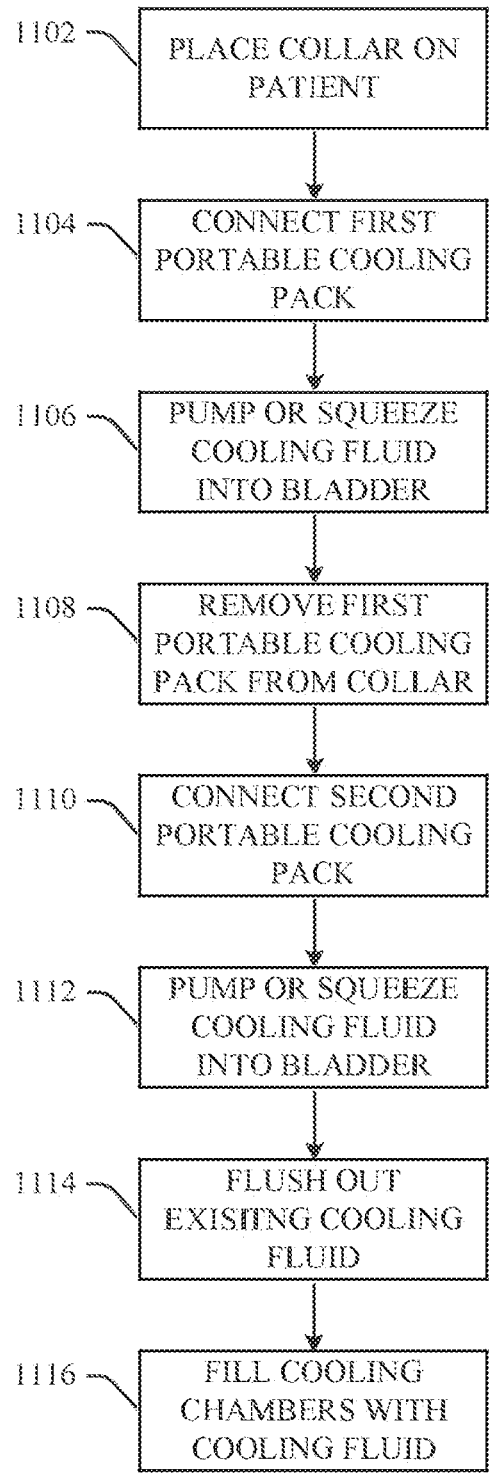
FIG. 11A illustrates a method of operating the cervical collar with portable fluid sources in accordance with aspects of the innovation.

For example, referring to FIG. 11A, at 1102, the cervical collar 500 is placed on the patient. At 1104, the port 902 of a first cooling pack is connected to the inlet port 534 of the cervical collar 500. At 1106, cooling fluid from the first cooling pack is squeezed into the bladder 506 of the cervical collar 500 thereby filling the cooling chambers 530. At 1108, once the cooling fluid from the first cooling pack reaches an undesirable temperature, the first cooling pack, which is empty, is attached to the outlet port 536 (or alternatively can be or stay connected to the inlet port 534). At 1110, a second cooling pack is attached to the port not in use (e.g., inlet port or outlet port) on the cervical collar 500. At 1112, cooling fluid from the second cooling pack is squeezed into the bladder 506. At 1114, the existing cooling fluid in the cooling chambers 530 from the first cooling pack is flushed out of the cooling chambers 530 and back into the first cooling pack. At 1116, cooling fluid from the second cooling pack fills the cooling chambers 530 with cooling fluid of a desired temperature.

In conjunction with the cooling packs 200, 900 previously described, the cervical collar 500 may include an indicator 538 (see FIG. 8) disposed on the retaining device 300 or on the bladder 506 (e.g., on at least one chamber 530 and/or at least one passageway 532) that indicates an approximate body (core or skin) temperature of the patient and/or an approximate temperature of the patient's cerebral vasculature and/or an approximate temperature of the cooling fluid in the fluid source 200, 900. In one embodiment, the indicator 538 may be an integrated portion of the cervical collar 500. In another embodiment, the indicator 538 may be a separate temperature sensitive device (e.g., sticker, etc.) that can be attached to the cervical collar 500 by the EMT personnel. The separate temperature sensitive device may be removable and re-attachable so that it can be moved to different locations on the cervical collar 500.

In one example, the indicator 538 can sequentially change color based on a change of a measurable event, such as but not limited to a change in a temperature of the cooling fluid. For example, the indicator 538 may be a first color (e.g., blue, dark blue, etc.) when the temperature of the cooling fluid is at a temperature (first temperature) that provides adequate cooling to the patient. As the temperature of the cooling fluid begins to lose its cooling effect (e.g., the cooling fluid begins to warm) or approaches (or reaches) a second temperature, the indicator 538 may turn a second color (e.g., orange). The second temperature can be any temperature that is higher than the first temperature (e.g., "x" degrees warmer than the first temperature). As the temperature of cooling fluid continues to warm or approaches (or reaches) a third temperature the indicator 538 may turn a third color (e.g., red) indicating that the cooling fluid is no longer providing adequate cooling to the patient. The third temperature can be any temperature that is higher than the second temperature and obviously higher than the first temperature (e.g., "y" degrees warmer than the second temperature, "z" degrees higher than the first temperature). The indicator 538 can provide a quick visual means for the EMT personnel to determine if the cooling pack 200 should be replaced or if additional cooling fluid should be pumped into bladder 506 with another cooling pack 900.

Similarly, when the warm cooling fluid is flushed out and replaced with cold cooling fluid, the color of the indicator can change back to the first color (e.g., blue, dark blue, etc.). In addition, if the cooling fluid is gradually cooled from a warm temperature, the color of the indicator can change back in sequence toward the first color. As the cooling fluid once again begins to warm, the above process can start over again.

In another example embodiment, the indicator 538 can change color based on a change of a measurable event, such as but not limited to, a passage of time where specific colors may represent an incremental passage of time. For example, the indicator 538 may be a first color (e.g., blue, dark blue, etc.) when the cooling fluid is first introduced. As time passes (e.g., 1, minute, 2 minutes, 3 minutes, etc.) the indicator 538 may change color to a second color (e.g., orange) to alert the EMT personnel how much time has passed. As more time passes, the indicator may turn a third color, fourth color, fifth color, etc.

In one example embodiment, the color change may be gradual, which may represent a passage of time in small increments (e.g., 1 minute increments, 2 minute increments, etc.). In another example embodiment, the color change may be more defined or abrupt (i.e., changing quickly from one color to another), which may represent a passage of time in larger increments (e.g., 5 minutes, 10 minutes, etc.). For example in one embodiment, orange may represent the passage of 5 minutes, red may represent the passage of 10 minutes, etc. In another example embodiment, every time the indicator changes color may represent an incremental passage of time (e.g., any color change represents a 5 minute increment, a 10 minute increment, etc.).

In this example embodiment, the indicator 538 can provide a quick visual means for the EMT personnel to determine how much time has passed. Since time is very crucial in traumatic head and neck injuries, the quick reference indicator provides the EMT personal a means to quickly determine how much time has passed.

In another example embodiment, the bladder 506 or any portion thereof, such as one or more cooling chambers 530 or one or more passageways 532, may act as the indicator. For example, the bladder 506 may be made from a material that changes color based on temperature, as previously described.

In another example embodiment, the outer shell 502 may be made from a transparent material or may include a viewing window that permits the EMT personnel to view the patient's neck for signs of trauma and/or view the indicator 538 described above. In still another embodiment, the bladder 506 may be made from a transparent material that allows the EMT personnel to see the cooling fluid. As such, the cooling fluid itself may act as the temperature indicator. For example, a color of the cooling fluid may change color as the temperature of the cooling fluid changes, as described above.

Figure 12:
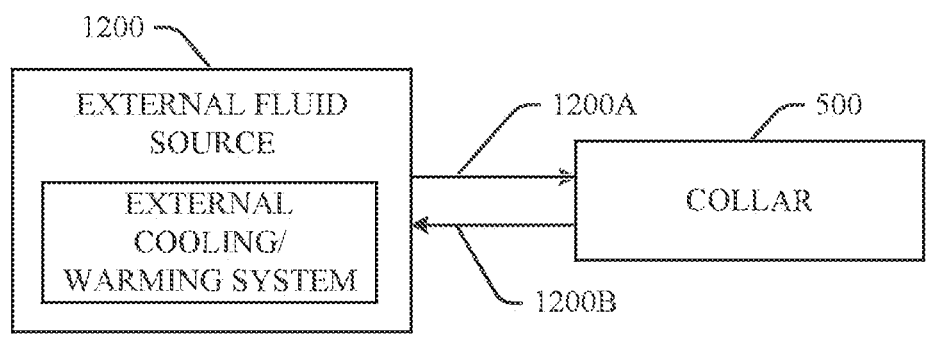
FIG. 12 is a block diagram illustration of an external fluid system fluidly communicating with the cervical collar in accordance with an aspect of the innovation.

Referring to FIG. 12, as mentioned above, another fluid source 1200 that the collar 500 can be connected to is an external cooling system 1200 that can continuously pump cooling fluid 1200A at a desired temperature through the bladder 506 thereby and flush out the warm cooling fluid 1200B, thereby providing a continuous circulation of cooling fluid at the desired temperature. Thus, the temperature of the cooling fluid can be regulated to maintain a predetermined temperature or adjust the temperature as desired. As such, this embodiment can be used to perform therapeutic hypothermia over an extended period of time to treat a particular type of injury or perform a particular type of procedure. For example, this example embodiment, as well as those described above, can be in the form of a wrap that employs the bladder 506 to treat injuries to the arms, shoulder, legs, knees, etc., as well as the neck area, where therapeutic hypothermia is required over an extended period of time.

Still referring to FIG. 12, it is to be understood that the innovative cervical collar disclosed herein can also be used as a warming device in appropriate medical applications. Thus, the cervical collar can be connected to the external fluid source 1200 that can pump warming fluid through the cervical collar as described herein. In one embodiment, the collar may be used for targeted temperature management in a hospital or medical environment. For example, the collar may be used to keep a patient warm during surgery or other medical procedure. In one embodiment, the collar may be used to modulate a patient's temperature post surgery. In one embodiment, the collar may be used for targeted temperature management in extreme environments, including in cold conditions.

Still referring to FIG. 12, the innovative cervical collar 500 can also be used as a compress. For example, in post-operative care, a practitioner can simply set the temperature of the fluid that does not induce hypothermia for the purpose of applying a cool or warm compress to the designated area. Still further, the practitioner can regulate the temperature of the fluid to transition between a cold compress and a warm compress and vice versa for therapeutic reasons.

Figure 12A:
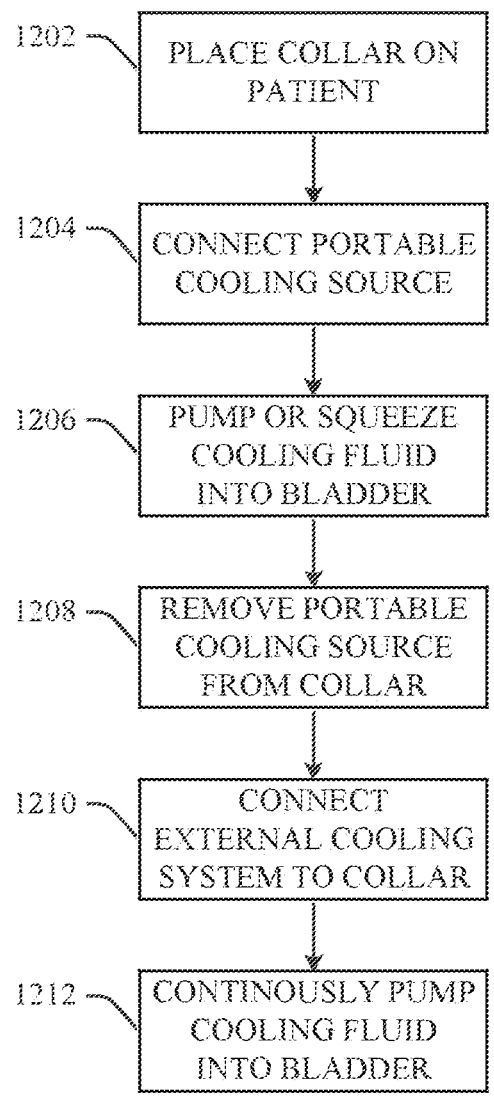
FIG. 12A illustrates a method of transitioning from a portable fluid source to an external fluid system in accordance with aspects of the innovation.

In addition, referring to FIG. 12A, the external cooling system 1200 in conjunction with the cooling packs 900 can provide a smooth transition from providing portable cooling fluid in the field to a continuous cooling system in a medical facility. Thus, once the patient arrives at a medical facility the cooling source can be transitioned from the portable cooling pack 900 described above to the external cooling system 1200 as illustrated in FIG. 12A. Specifically, at 1202, the cervical collar is placed on the patient. At 1204, the portable cooling pack 900 is connected to the inlet port 534. At 1206, cooling fluid from the cooling pack 900 is pumped or hand squeezed into the bladder 506 thereby filling the cooling chambers 530. At 1208, once the patient arrives at a facility (e.g., medical facility) that has an external cooling system 1200, the portable cooling pack 900 is removed from the inlet port 534. At 1210, the external cooling system 1200 is connected to the cervical collar 500. At 1212, cooling fluid is pumped into the bladder 506, which flushes out the existing cooling fluid inside the cooling chambers 532.

It is to be understood that the transition process illustrated in FIG. 12A can also be from the continuous cooling system to the portable cooling packs. For example, if a trauma patient is connected to the continuous cooling system in a medical facility that is not capable of handling trauma patients, the patient can be transitioned from the permanent system to the portable cooling packs in order to transport the patient to a trauma facility.

Figure 5:
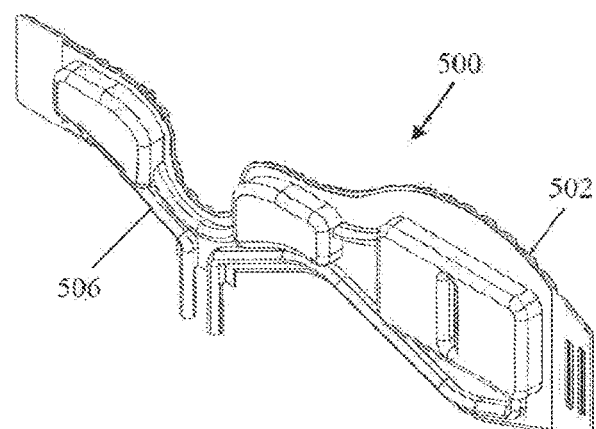
FIG. 5 is a perspective view of another embodiment of a cervical collar incorporating a cooling device in accordance with aspects of the innovation.
Figure 13:
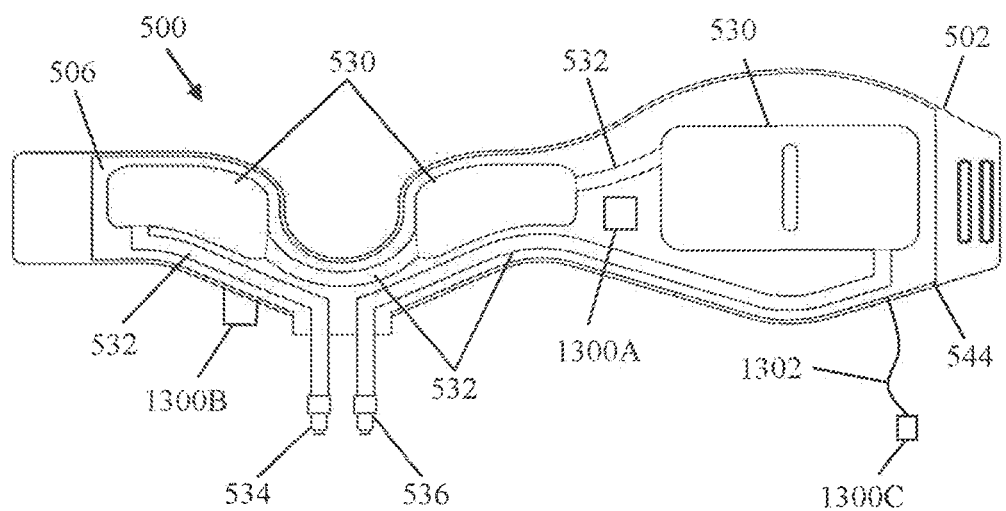
FIG. 13 is a front view of the cervical collar of FIG. 5 incorporating a temperature sensing device in accordance with an aspect of the innovation.

Referring to FIG. 13, the example embodiment of the cervical collar 500 illustrated in FIG. 5 above may include one or more temperature sensors 1300A or 1300B or 1300C that may measure a body (or core) temperature of the patient and/or a cerebral vasculature temperature of the patient. Although like features are referenced in FIG. 13, a description of such features will not be repeated for simplicity. The temperature sensors 1300A-C illustrated in FIG. 13 can be any type of temperature sensor, such as but not limited to, an infrared sensor, a stick tab sensor, etc. The presence of a temperature sensor allows medical personal to not only monitor, but also regulate the patient's body and/or cerebral vasculature temperature via the external cooling system mentioned above. Thus, to increase or decrease either temperature of the patient, the flow rate of the external cooling system is either increased or decreased respectively (alternatively, the temperature of the cooling can be adjusted as opposed to the flow rate). Thus, medical personnel are able to maintain the patient's body or cerebral vasculature temperature at a target temperature to thereby minimize the traumatic effect to the patient. It is to be understood, that any type of sensor that measures a physical characteristic of the patient may be included in the cervical collar. For example, in lieu of or in addition to a temperature sensor, a sensor may be included that measures the patient's pulse, hydration, perspiration, blood pressure or other vitals, etc., all of which can be employed in a system's logic analysis or by a medical or training professional in order to trigger action upon the user or other pertinent diagnostics.

In one example embodiment, the temperature sensor 1300A can be disposed on the bladder 506 such that when the cervical collar 500 is placed on the patient, the temperature sensor 1300A is already positioned to monitor the body temperature of the patient.

In another example embodiment, the temperature sensor 1300B can have a tab like configuration that attaches to a bottom edge 546 (as shown in FIG. 13) of the cervical collar 500. Thus, when the cervical collar 500 is placed on the patient, the temperature sensor 1300B is already positioned to monitor the body temperature of the patient. It is to be appreciated that the tab like temperature sensor 1300B can attach to a top or side edge of the cervical collar 500.

In still yet another example embodiment, the temperature sensor can be attached to any location (e.g., the outer shell 502, the bladder 506, etc.) on the cervical collar 500 via a tether 1302, as illustrated by temperature sensor 1300C. Once the cervical collar 500 is in place the temperature sensor 1300C can be placed on the patient at any convenient location, such as but not limited to, the forehead, neck area, etc.

Figure 14:
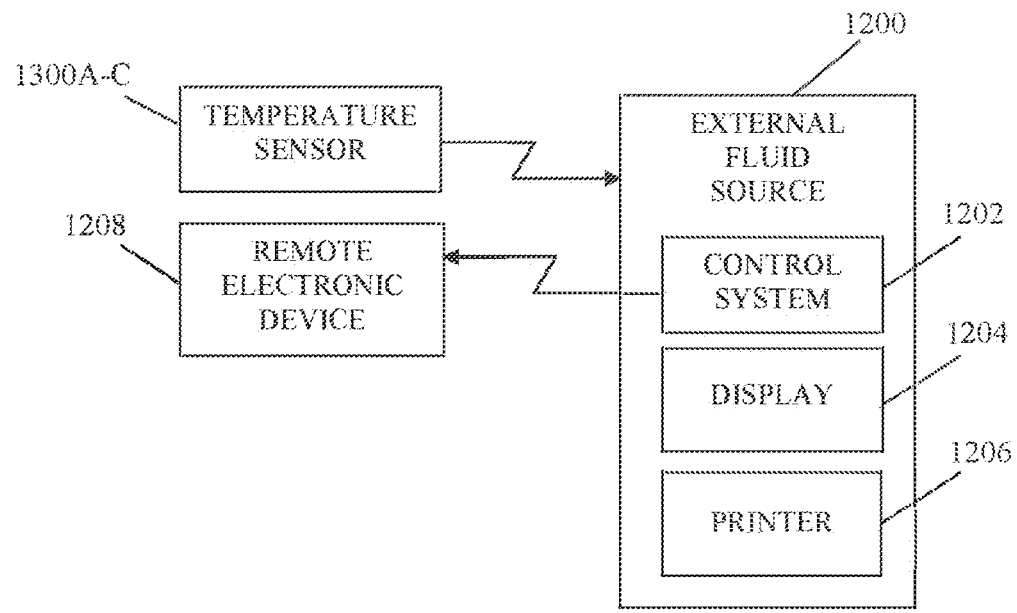
FIG. 14 is a block diagram illustration of the external cooling system communicating with peripheral electronic devices in accordance with an aspect of the innovation.

Referring to FIG. 14, in another embodiment, the temperature sensor 1300A-C can communicate with the external fluid source 1200 to automatically control the flow rate of the cooling fluid, thereby automatically adjusting the body temperature of the patient. For example, the body temperature of the patient can be continuously transmitted to a control system 1202 of the external fluid source 1200. The control system 1202 can then adjust the flow rate of the cooling fluid to adjust the body temperature until a desired target body temperature is reached. Further, the control system 1202 can continually or incrementally adjust the flow rate of the cooling fluid to gradually increase or decrease the patient's body temperature as desired.

In another example embodiment, the control system 1202 can be programmed to automatically adjust the flow rate of the cooling fluid to reach a target temperature based on several factors, including but not limited to, the patient's characteristics (e.g., the patient's health history if available, the patients physical make-up (e.g., height, weight, etc.)), environmental conditions (e.g., ambient temperature, etc.), etc.

Still referring to FIG. 14, patient information, such as but not limited to, patient's body temperature, flow rate of cooling fluid, patient's pulse, etc., may be visually displayed via a display 1204 associated with the external cooling system or printed via a printer 1206 associated with the external cooling system 1200. Further, the information may be transmitted from the control system 1202 to a remote location (e.g., medical facility) or to an electronic device 1408, such as but not limited to, a mobile phone, a tablet, a PDA, a computer, etc.

Figure 14A:
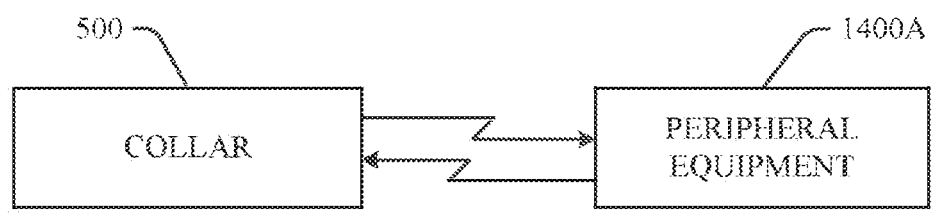
FIG. 14A is a block diagram illustration of the cervical collar communicating with peripheral electronic devices in accordance with an aspect of the innovation.

Referring to FIG. 14A, the innovative cervical collar 500 can be configured as part of a system that allows the cervical collar 500 to communicate with peripheral medical and non-medical equipment 1400A (e.g., fluid sources, thermal imaging devices (camera), temperature devices, printer, computer, etc.). Thus, the practitioner can program the peripheral equipment to set certain parameters. For example, the practitioner can program a temperature of the fluid, a flow rate of the fluid, a temperature of the patient's cerebral vascular and/or core, etc. Thus, the practitioner can easily achieve desired parameters by simply programming the peripheral equipment in use with the cervical collar 500. The communication between the cervical collar 500 and the peripheral equipment can be wired or wireless (e.g., RF, Bluetooth, etc.).

Figure 15:
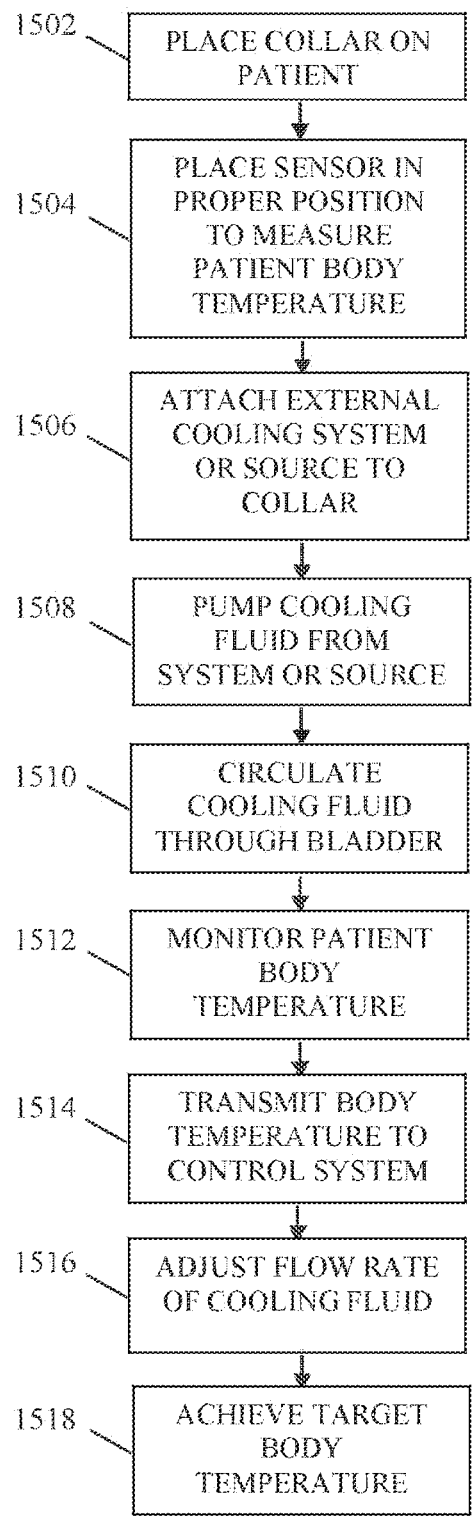
FIG. 15 illustrates a method of operating the cervical collar of FIG. 13 in accordance with aspects of the innovation.

Referring to FIG. 15, a method of using the collar 500 incorporating the bladder 506 will now be described. At 1502, the collar 500 is placed on the patient. At 1504, the sensor is properly placed to monitor the patient's temperature. At 1506, the external cooling system or source is connected to the bladder via the inlet and outlet ports 534, 536. At 1508, cooling fluid from the external cooling system or source is pumped into the bladder 506. If desired, at 1510, the cooling fluid can be continuously circulated through the bladder 506. At 1512, the patient's body temperature is monitored. At 1514, the body temperature is transmitted to the control system. At 1516, the flow rate of the cooling fluid is adjusted to regulate the patient's body temperature. At 1518, the target body temperature is achieved.

Figure 15A:
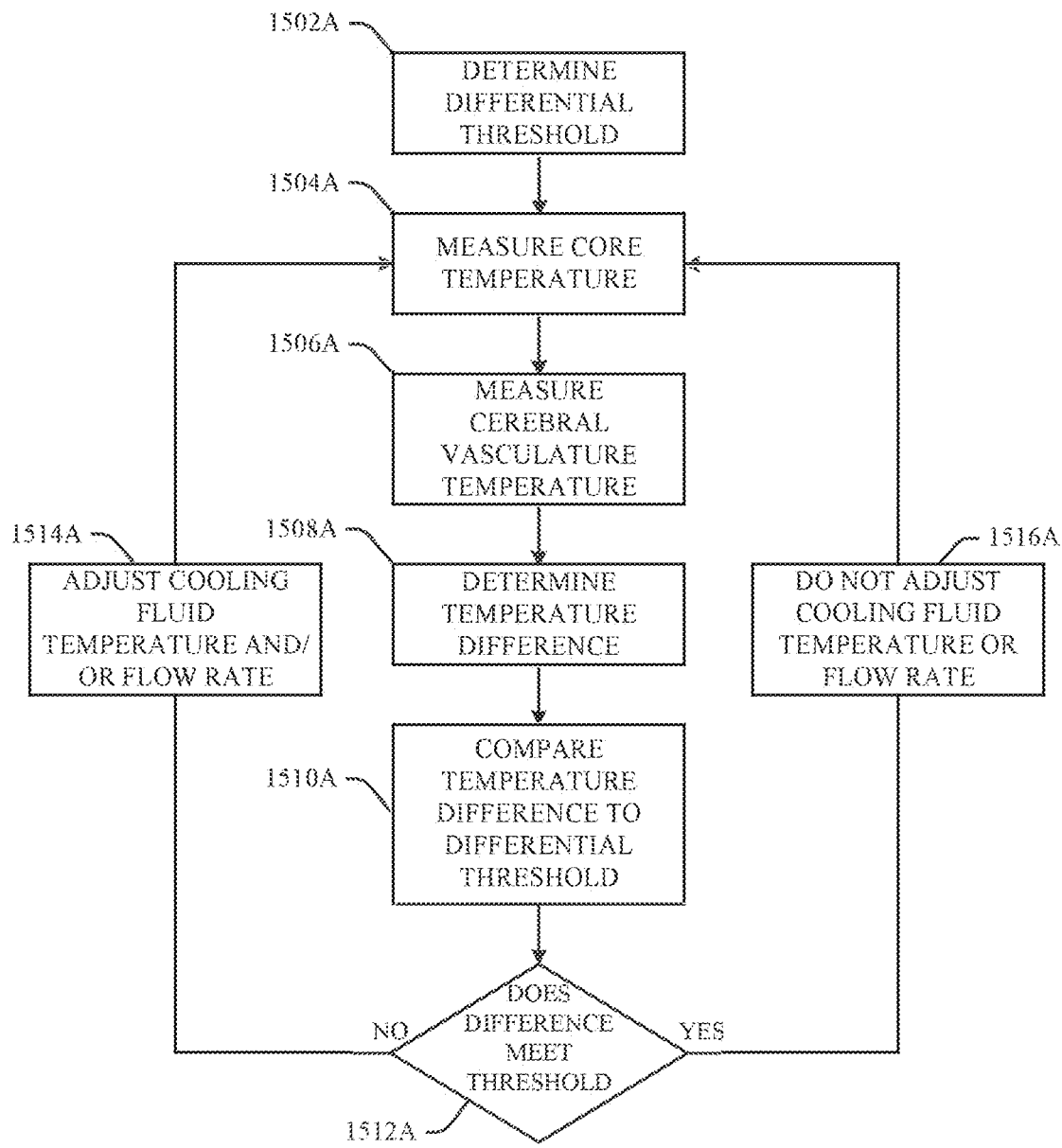
FIG. 15A illustrates a method of adjusting cooling fluid in the cervical collar in accordance with an aspect of the innovation.
Figure 16:
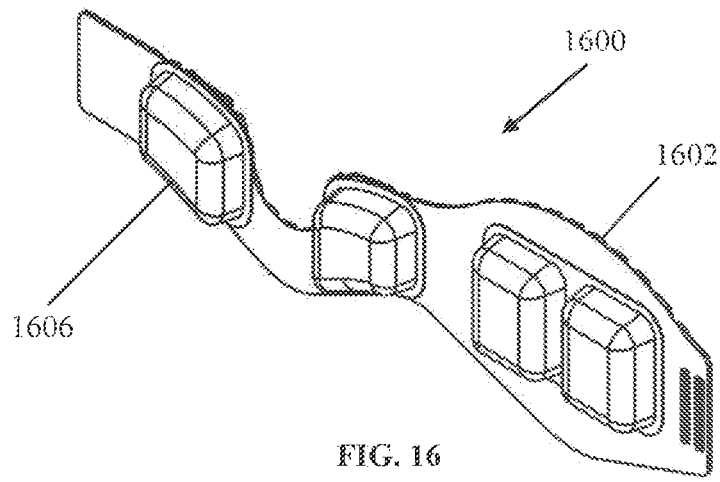
FIG. 16 is a perspective view of another embodiment of a cervical collar incorporating a cooling device in accordance with aspects of the innovation.

Referring to FIG. 15A, as mentioned above, in another example embodiment, the cervical collar 500 can include multiple temperature sensors to measure the patient's body (or core or skin) temperature and/or the temperature of the patient's cerebral vasculature. For example, the core temperature, the cerebral vasculature temperature, and/or the difference between the two can be used to determine if the temperature and/or flow rate of the cooling fluid should be adjusted. For example, once the cervical collar 500 is placed on the patient and the cooling fluid is circulating through the collar, at 1502A a differential threshold can be predetermined. At 1504A, the core temperature of the patient is measured and recorded. At 1506A, the temperature of the cerebral vasculature of the patient is measured and recorded. At 1508A, a temperature difference between the core temperature and the cerebral vasculature is determined. At 1510A, the temperature difference is compared to the differential threshold. If at 1512A the temperature difference does not meet the differential threshold, the process goes to 1514A and the temperature and/or the flow rate of the cooling fluid is adjusted. The process then loops back to 1504A and the process is repeated till the temperature difference meets the differential threshold. When the temperature difference meets the differential threshold then at 1512A, the process goes to 1516A and the temperature or the flow rate of the cooling fluid is not adjusted. The process then loops back to 1504A and the process is repeated to insure that the temperature difference continues to meet the differential threshold.

FIGS. 16-19 represent another example embodiment of a cervical collar 1600 (hereinafter "collar") incorporating a cooling device. The collar 1600 includes an outer shell 1602, an adjustable support (not shown), and a cooling device 1606. It is to be appreciated that while the collar 1600 can be used for inducing hypothermia, the collar 1600 can also be used as a standard cervical collar when a patient does not require therapeutic hypothermia.

Figure 17:
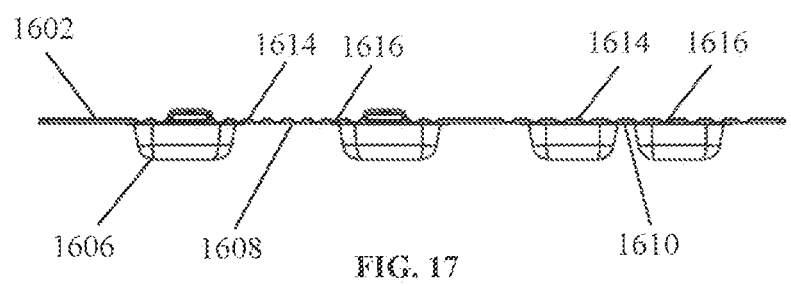
FIG. 17 is a top view of the cervical collar of FIG. 16 in accordance with aspects of the innovation.
Figure 18:
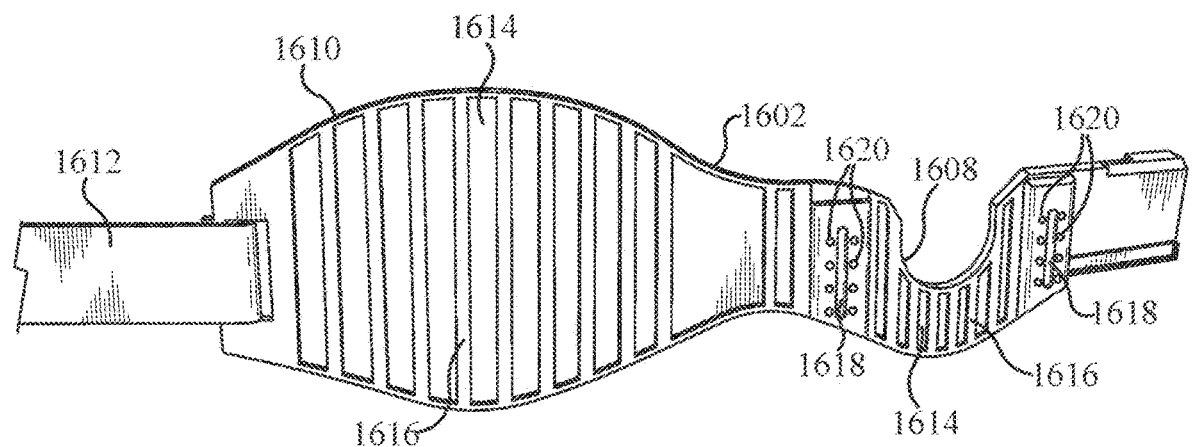
FIG. 18 is a rear view of the cervical collar of FIG. 16 in accordance with aspects of the innovation.

Referring to FIGS. 17 and 18, the outer shell 1602 includes a front portion 1608 fixedly coupled to a back portion 1610 on one side and a fastening device 1612 attached to the back portion 1610 and removably coupling the front and back portions 1608, 1610 on an opposite side. The features of the fastening device 1612 are similar to the fastening device 108 described above and, as such, will not be repeated.

The outer shell 1602 is made from a flexible plastic material, such as but not limited to polyethylene, polystyrene, etc. Further, both the front and back portions 1608, 1610 include multiple panels 1614 each connected by hinged portions 1616 that further facilitate in the flexibility of the outer shell 1602. This configuration allows EMT personnel to control the flexibility of the collar 1600 and easily adjust the collar 1600 to fit the patient. In addition, the flexibility characteristic allows the collar 1600 to be packaged in a flat state thereby optimizing volume space for shipping and/or storage purposes. The front portion 1608 of the outer shell 1602 further includes multiple slots 1618 and multiple recesses 1620 disposed on each side of each slot 1618. The multiple slots 1618 and multiple recesses 1620 facilitate attachment and adjustment of the support to the collar 1600 subsequently described.

The support is used to support the patient's chin and is adjustable to conform to the patient. The support includes attachment legs that attach the support to the front portion 1608 and a connection part connecting distal ends of the attachment legs. The connection part serves to support the patient's chin. Multiple slots 1618 are defined in the front portion 1608 to receive the attachment legs to thereby connect the support to the collar 1600. The support can be adjusted by sliding each attachment leg in each slot 1618 to a desired position. The attachment legs engage recesses 1620 defined on each side of each slot 1618 to lock the support in its desired position.

As mentioned above, the connection part provides a connection between the distal ends of the attachment legs. The connection point between the attachment legs and the connection part is hinged to facilitate packaging. Specifically, when the collar 1600 is packaged in a flat state, mentioned above, one attachment leg is disconnected from the collar 1600 and laid in a flat state. This is possible because of the hinged connection.

Figure 19:
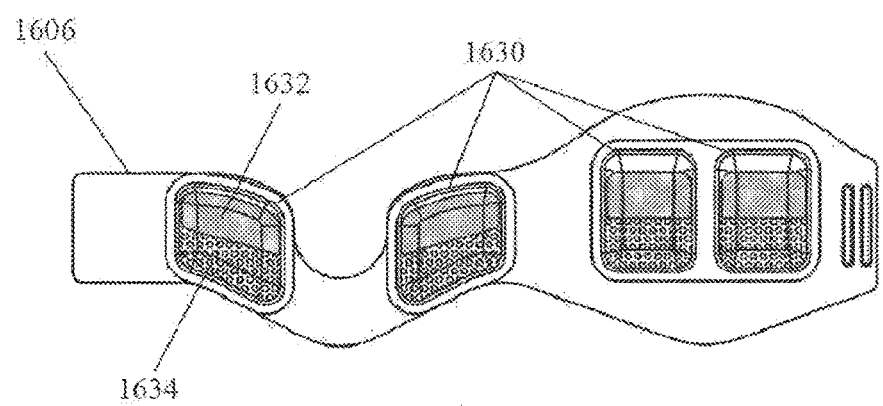
FIG. 19 is a front view of the cervical collar of FIG. 16 in accordance with aspects of the innovation.

Referring to FIG. 19, the cooling device 1606 includes one or more cooling packs 1630 integrated into an interior of the collar 1600. The cooling pack(s) 1630 can be strategically disposed at essential locations on the cervical collar 1600 to target the areas of the neck described above. For example, the cooling pack(s) 1630 can be located on the front portion 1608 to target the carotid arteries and/or on the back portion 1610 to target the spinal cord area. The cooling pack(s) 1630 can be any type of cooling pack, such as but not limited to chemical pack. For example, the cooling pack(s) 1630 can be a granule-activation packet uses a fluid 1632, such as but not limited to, water and a chemical 1634, such as but not limited to, ammonium nitrate that when mixed together create a cooling fluid. Once the cooling packs 1630 are activated, the cervical collar 1600 can be placed on the patient to provide the desired therapeutic hypothermia to essential portions of the neck area described above.

In other embodiments, the cervical collar disclosed herein can include a marking(s) and/or be made from different colors where the markings and/or colors represent a particular attribute. For example, the marking(s) and/or color may represent a type of injury that the cervical collar should be used on, a size of the cervical collar, a cooling fluid flow rate, if the cervical collar is used as a cooling device (e.g., the color blue) or used as a warming device (e.g., the color red), etc. In addition, the cervical collar may include multiple markings or different parts of the cervical collar may be made of different colors where certain combinations of markings and/or colors (e.g., the bladder may be one color and the outer shell may be a different color) represent one or more attributes of the cervical collar, such as those listed above.

For example, as mentioned above, the cervical collar can selectively cool the cerebral vasculature relative to the whole body. Thus, the cervical collar may include markings and/or be color coded to indicate that the cervical collar can be used to electively cool the cerebral vasculature. As medical professionals have a number of medical devices at their disposal, such as neck braces or other traditional cervical collars, the innovative cervical collar that includes markings and/or is color coded provides the medical professionals a vehicle to quickly identify the proper medical device required to treat the patient in circumstances where time is of the utmost importance.

Figure 20:
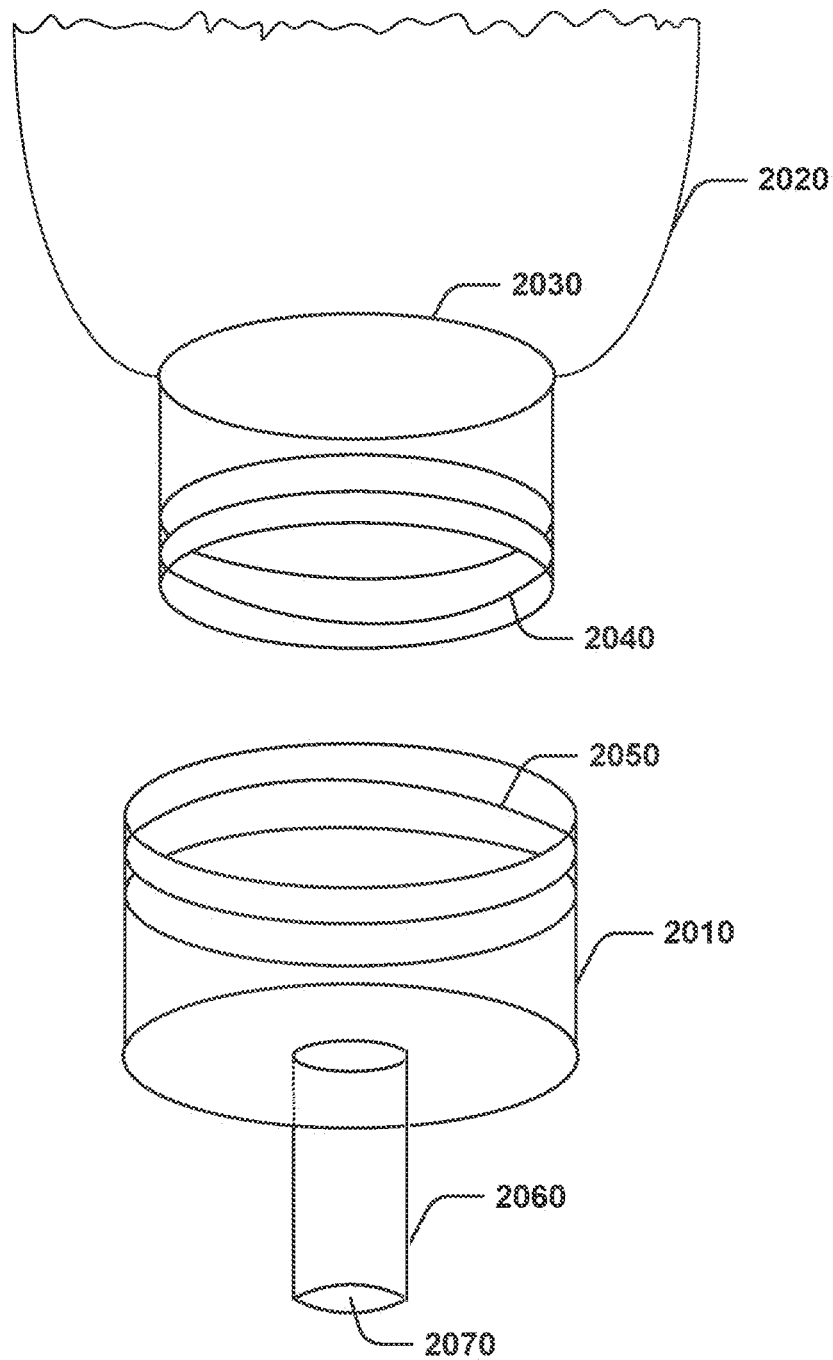
FIG. 20 illustrates a cooling cap collar 2010 in accordance with aspects of the innovation.

FIG. 20 illustrates a cooling cap collar 2010 that is adaptable to accept heating/cooling sources or a portable cooling pack 2020. While a "cooling" pack is described herein, it is to be understood that embodiments can also be employed that "warm" or otherwise alter temperature as desired. The portable cooling pack 2020 includes an opening 2030 that acts as an outlet port through which cooling liquid can pass through. The portable cooling pack 2020 can be a bottle that uses a fluid, such as but not limited to, water, soda, sports drink, and/or the like. In some embodiments, the portable cooling pack 2020 can be used to mix water or liquid with a chemical to create a cooling (or warming) fluid. In some embodiments, the portable cooling pack 2020 is a water bottle, soda bottle, sports drink bottle, and/or the like. The portable cooling pack 2020 can include a threading 2040 on the interior or exterior of the opening 2030. The threading 2040 can be used to connect the portable cooling pack 2020 to the cooling cap collar 2010. The cooling cap collar 2010 can include a second threading 2050 that can interact (e.g. twist) with the threading 2040 of the portable cooling pack 2040 to couple the cooling cap collar 2010 with the portable cooling pack 2040. The example embodiment describes threads such that the cooling cap collar 2010 and the portable cooling pack 2020 can twist together to couple to one another. It is appreciated that other coupling embodiments are contemplated such as, but not limited to, snap coupling, tension coupling, rubber coupling, adhesive couple, and/or the like.

The cooling cap collar 2010 can include a nozzle outlet 2060 such that fluid can pass from the portable cooling pack 2020 to the bladder 506 (not shown) via the cooling cap collar 2020. The nozzle outlet 2060 can include an opening 2070 for passing the fluid to the bladder 506. In some embodiments, the nozzle outlet 2060 includes threading to twist or interact with the inlet port 534. In other embodiments, the nozzle outlet 2060 can include snap means, puncture means, push flow regulation means, and/or the like to couple with the inlet port 534 such that cooling fluid can pass to the bladder 506. When the portable cooling pack 2020 is coupled to the cooling cap collar 2010 and the cooling cap collar 2010 is coupled with the inlet port 534 of the bladder 506, the water and/or cooling fluid from the portable cooling pack 2020 can then be mechanically pumped or hand squeezed into the bladder 506 via the inlet port 534 and into each chamber 530 via the passageways 532, as described above.

In addition, once the cooling fluid inside the bladder 506 begins to warm, the empty portable cooling pack 2020 can be attached to the outlet port 536 and a new portable cooling pack 2020 can be attached to the inlet port 534. The cooling fluid from the new portable cooling pack 2020 can then be pumped or squeezed into the bladder 506 thereby forcing or flushing the warm fluid out of the bladder 506 through the outlet port 536 and back into the original cooling pack 2020. Thus, cooling fluid can essentially be continuously pumped through the collar 506 by a person who do not have access to a continuous external cooling system in the field.

Figure 21:
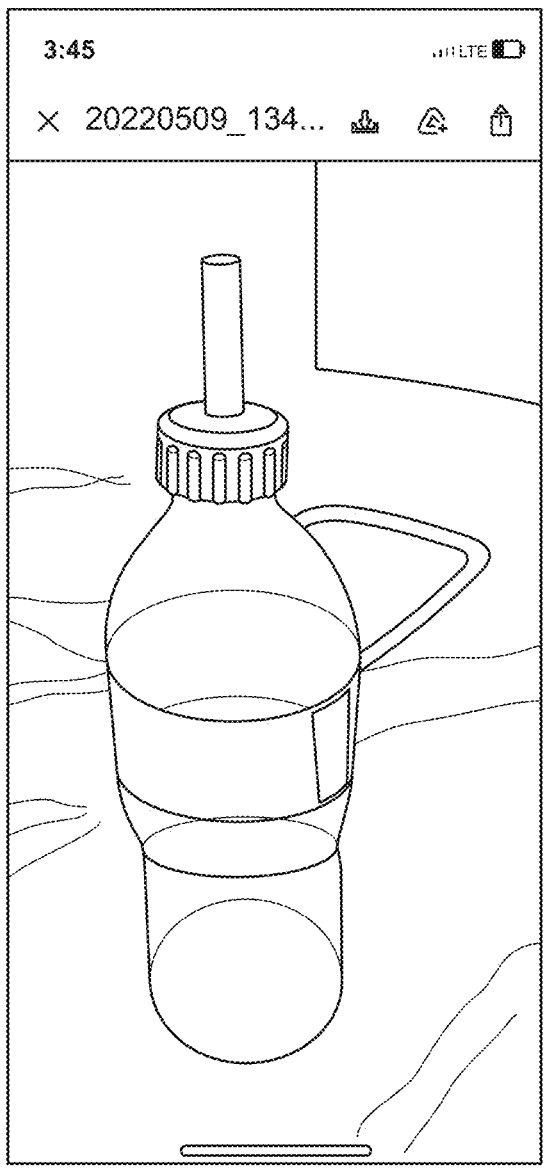
FIG. 21 illustrates an example embodiment of a cooling cap collar 2010 coupled with a portable cooling pack 2020 in accordance with aspects of the innovation.
Figure 22:
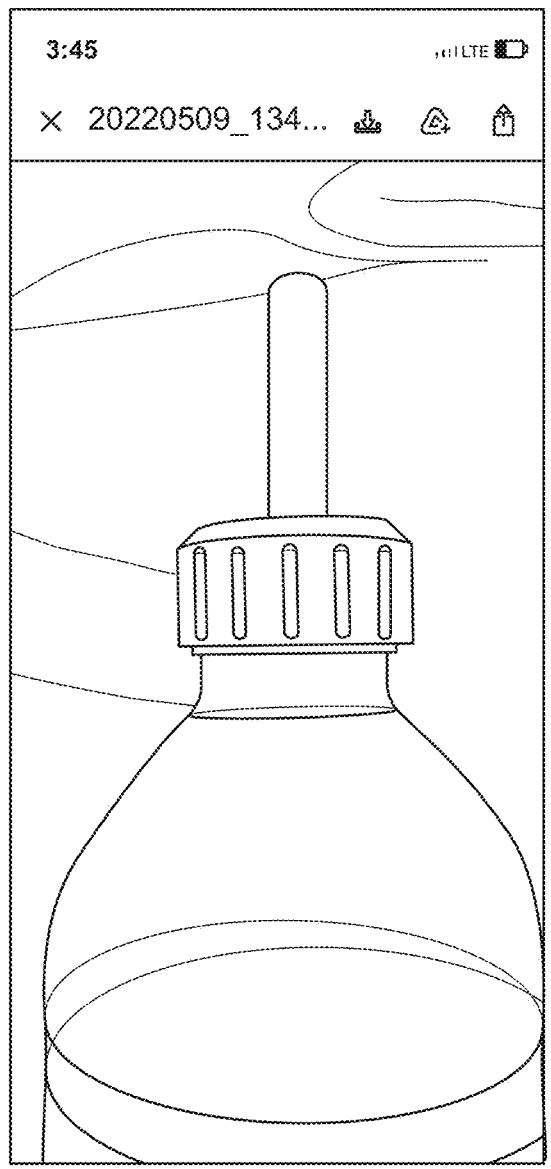
FIG. 22 illustrates a close up view of the example embodiment of the cooling cap collar 2010 coupled with the portable cooling pack 2020 in accordance with aspects of the innovation.

FIG. 21 illustrates an example embodiment of a cooling cap collar 2010 coupled with a portable cooling pack 2020. In the example embodiments, the portable cooling pack 2020 is a bottled water container that can hold water or cooling liquid. FIG. 22 illustrates a close up view of the example embodiment of the cooling cap collar 2010 coupled with the portable cooling pack 2020.

Figure 23:
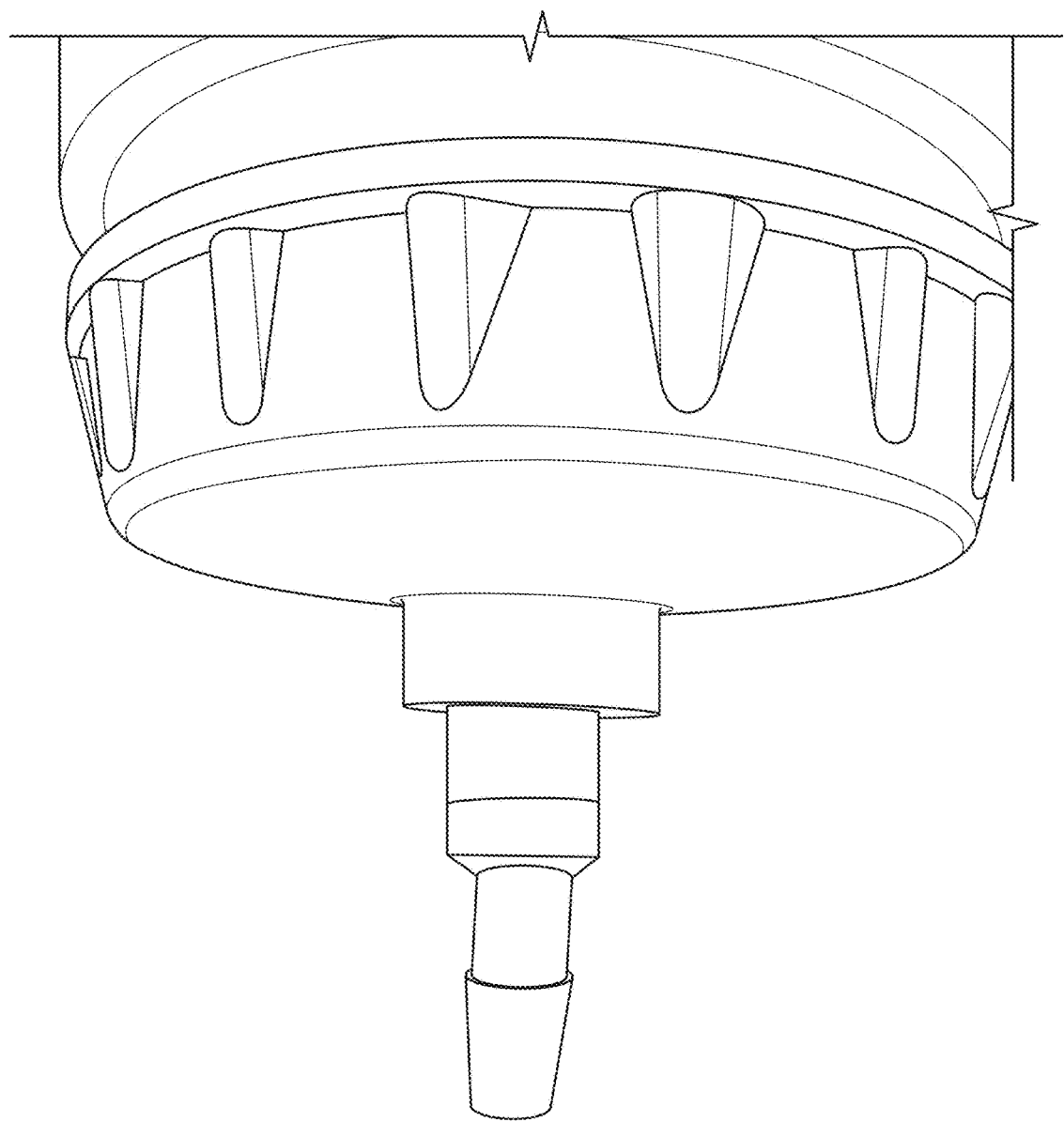
FIG. 23 illustrates an example embodiment of a cooling cap collar 2020 that couples with a sports bottle pull tap or nozzle in accordance with aspects of the innovation.
Figure 24:
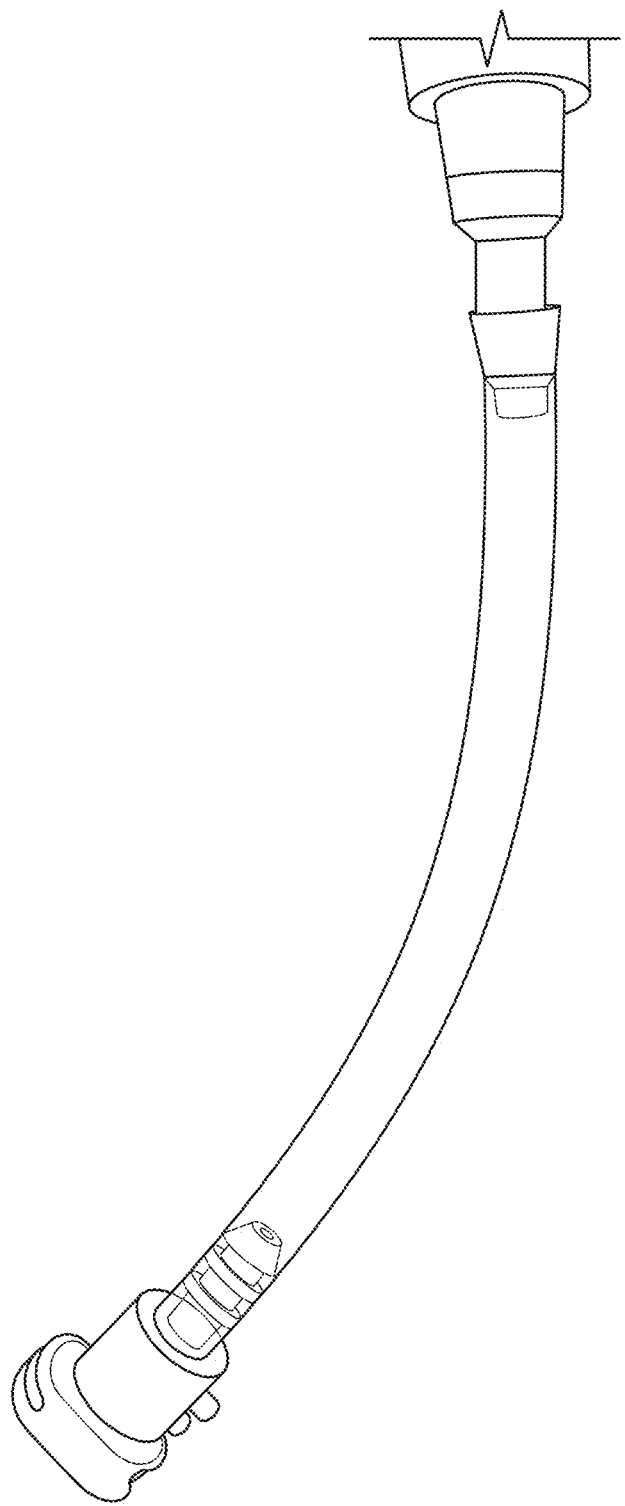
FIG. 24 illustrates an example embodiment of a cooling cap collar 2020 that couples with a sports bottle pull tap in accordance with aspects of the innovation.
Figure 25:
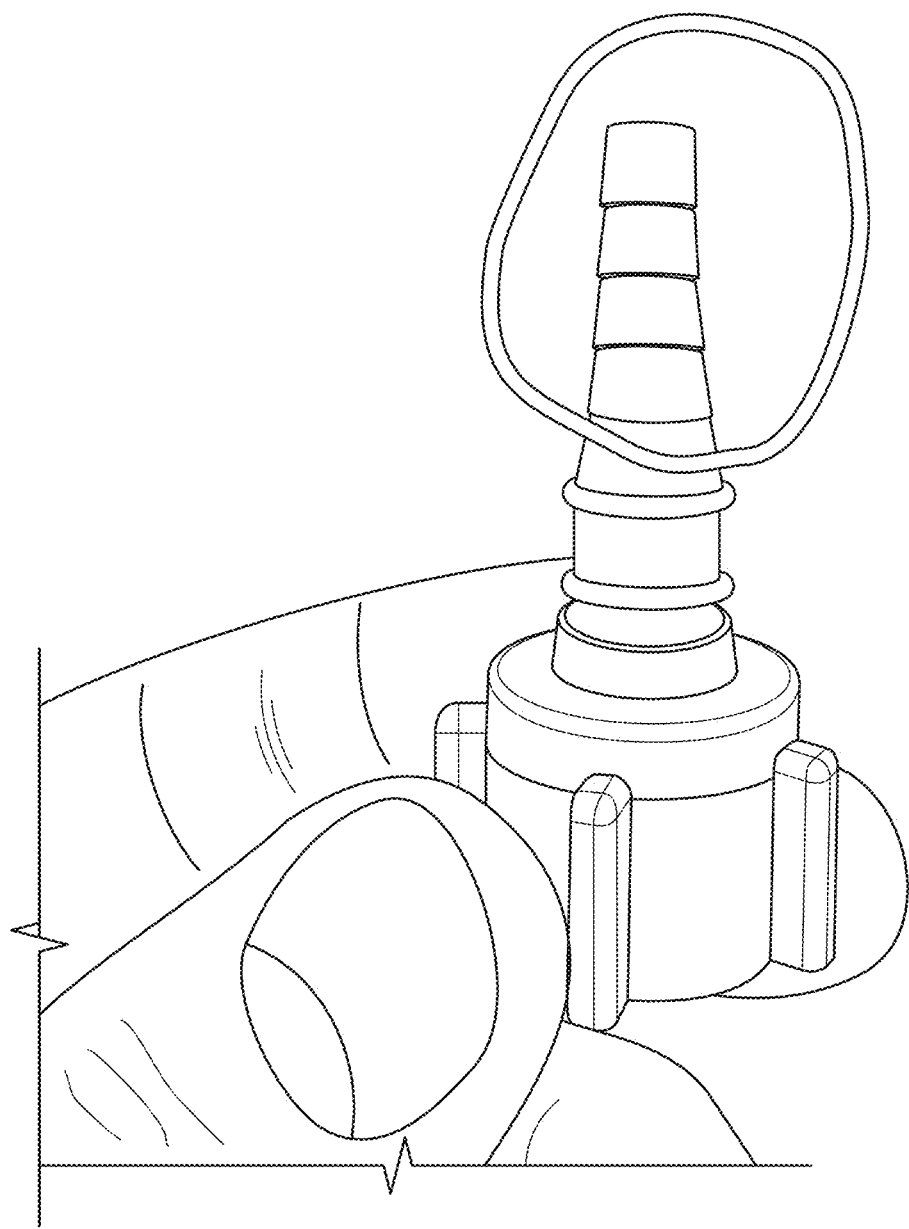
FIG. 25 illustrates an example embodiment of a snap cooling collar cap 2020 in accordance with aspects of the innovation.

FIG. 23 illustrates an example embodiment of a cooling cap collar 2020 that couples with a sports bottle pull tap or nozzle. In another embodiments, the cooling cap collar 2020 can replace the sports bottle lid and couple with the sports bottle body. FIG. 24 illustrates an example embodiment of a cooling cap collar 2020 that couples with a sports bottle pull tap or replaces the sports bottle lid and further adapts at an outlet nozzle with a port that acts as both an inlet port and an outlet port to provide and release cooling liquid via the same port of the bladder. FIG. 25 illustrates an example embodiments of a snap cooling collar cap 2020. The snap cooling collar cap 2020 can be inserted into the inlet port of the bladder. The snap cooling collar cap 2020 includes ridges that progressively are larger to form a seal with the inlet port that is water tight.

Figure 26:
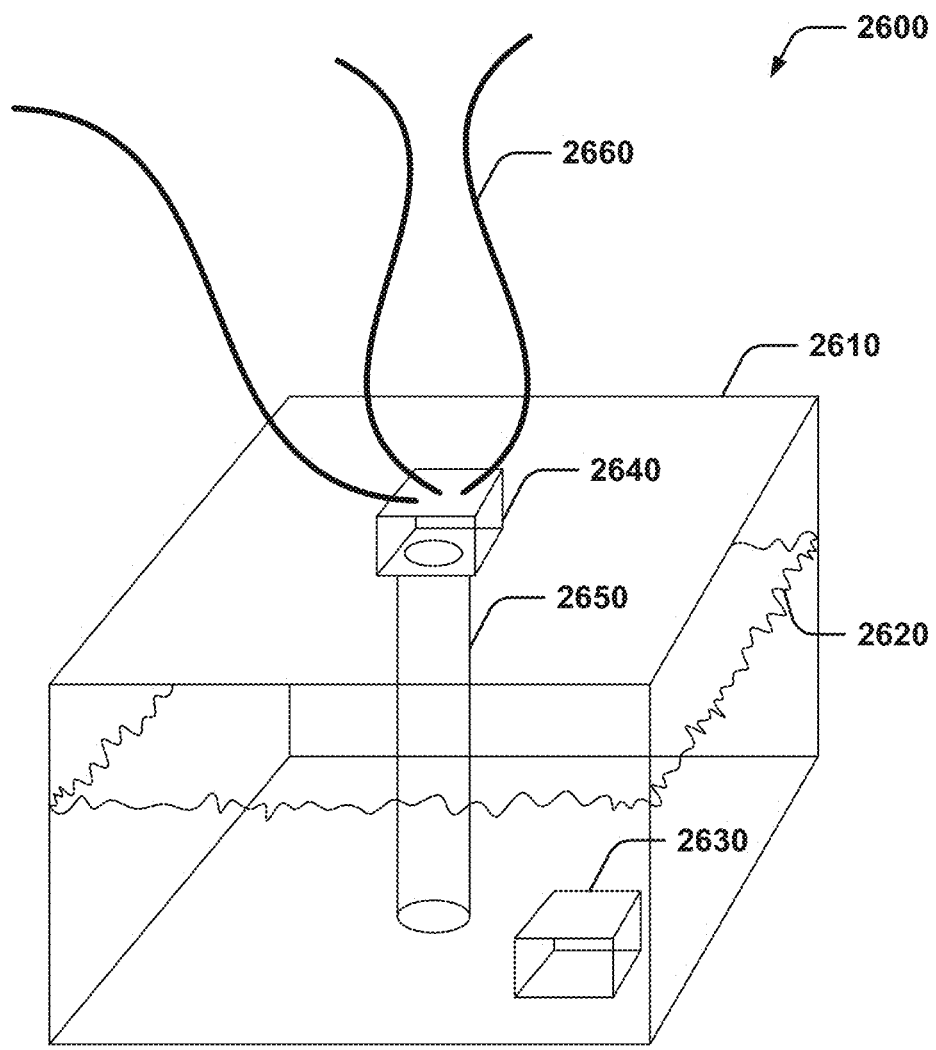
FIG. 26 illustrates an example embodiment of a cooling pump in accordance with aspects of the innovation.

Turning now to a discussion of other mechanisms by which temperature controlled fluid and/or gas can be generated and transmitted or circulated, FIG. 26 illustrates an example temperature control unit or pump 2600 that is adaptable to dispense heating/cooling liquid to one or more devices (e.g., cervical collars, wraps, etc.) simultaneously. As will be understood upon a review of the drawings, in aspects, the temperature control unit 2600 can be equipped with a manifold or splitter that can facilitate multiple outlets from the temperature control unit. As shown, the temperature control unit 2600 includes a reservoir 2610 capable of retaining a volume of fluid 2620. In other words, the reservoir 2610 can retain liquid 2620 such that the liquid 2620 can be temperature controlled as desired. In embodiments, the liquid 2620 can be a heating liquid, cooling liquid, and/or the like. For example, the liquid 2620 can be water or a water-based solution as well as most any chemical composition.

In some embodiments, the reservoir 2610 can include a filling opening, a draining opening, a removable bladder, a liquid source, a chemical source, and/or the like. These aspects will be understood by those skilled in the art. In other words, it will be appreciated that the unit can be filled (e.g., via a garden hose) as well drained (e.g., for transport, etc.) Further, a removable (or portable bladder) can be employed, for example to fill the unit in the event a liquid source is not readily available/present.

In some embodiments, the reservoir 2610 can be made of insulated plastic, double walled insulation, other insulation solutions, and/or the like. It will be appreciated that the insulation can assist in maintaining a desired output temperature. In other embodiments, the reservoir 2610 can be plastic, metal, foam, other suitable material (or combinations of materials), and/or the like.

The temperature control unit 2600 can include a control element 2630. The control element 2630 can facilitate movement (e.g., push, pull, mix, pressurize, etc.) the liquid 2620 within the reservoir 2610. In non-liquid aspects, the circulation element can facilitate pressurizing or otherwise pumping temperature controlled gas to a distribution manifold 2640 for output to the aforementioned therapeutic and/or medical devices (e.g., collar(s), wrap(s), etc.) The control element 2630 can heat or cool the liquid 2620 (or gas) as desired. The element 2630 can be powered via a battery, plug in outlet, solar, external power source, internal power source, and/or the like.

The control element 2630 can be settable to a temperature via a thermostat, regulator or other suitable control. In some embodiments, the control is mounted on the reservoir 2610 and can provide settings such as dispensing mode, desired temperature, timing, flow rate, on/off timing sequence(s), and/or the like. In some embodiments, the control element 2630 may include a wireless connection such that the element 2630 can be controlled via a mobile phone application, remote interface, Bluetooth connection, WIFI, radio frequency (RF), ultra wide band (UWB), and/or the like.

In some embodiments, the control element 2630 can include fins dispersed into the reservoir 2610 to efficiently control the temperature of the liquid 2620. In other embodiments, the control element or unit 2630 can include a circulator module that facilitates distribution of temperature controlled liquid (or air) throughout (and from) the temperature control unit 2600.

As discussed above, the temperature control unit 2600 can include a distribution manifold or plurality of manifolds 2640 that facilitate multiple outputs or outlets 2660 from the temperature control unit 2600. In addition to providing multiple outlets 2660, the manifold 2640 also facilitates detachment of the temperature control unit 2600 without disruption of the heating and/or cooling functions.

Figure 27:
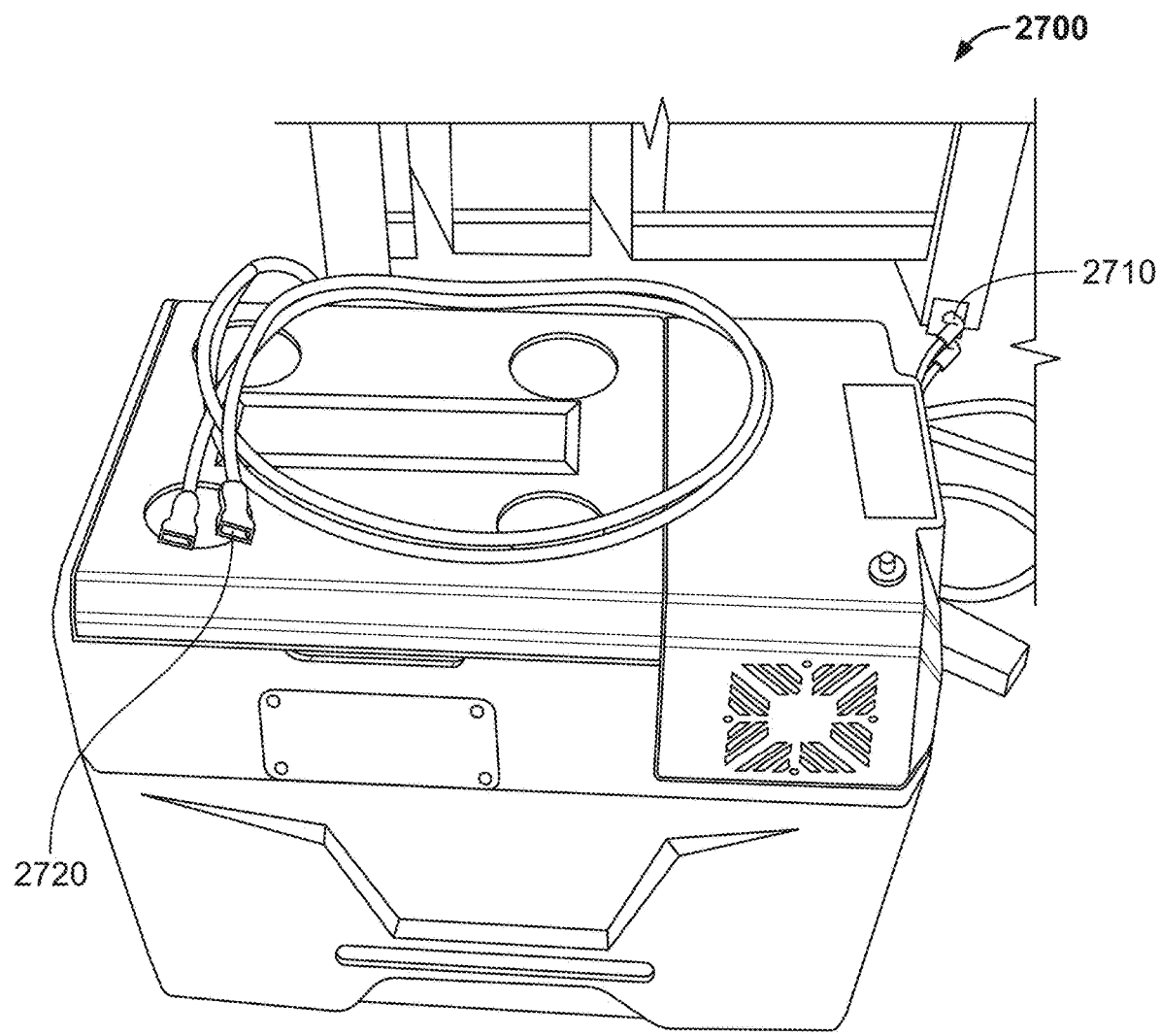
FIG. 27 illustrates an example embodiment of a cooling pump in accordance with aspects of the innovation.

FIG. 27 illustrates an example embodiment of a temperature control unit 2700 in accordance with aspects of the innovation. In the example embodiment, the temperature control unit 2700 is a portable refrigerating container that can retain liquid (e.g., water or cooling liquid) in an internal reservoir as described supra. In operation, temperature controlled liquid (e.g., chilled water) can be pumped via multiple output connectors 2710. Output hoses 2720 can be connected to the output connectors 2710 on one end and onto the therapeutic or medical device (e.g., collar(s), wrap(s), etc.) on the other end. Additionally, as described herein, the unit can be powered via an external or internal power source (e.g., a rechargeable portable battery pack).

Figure 28:
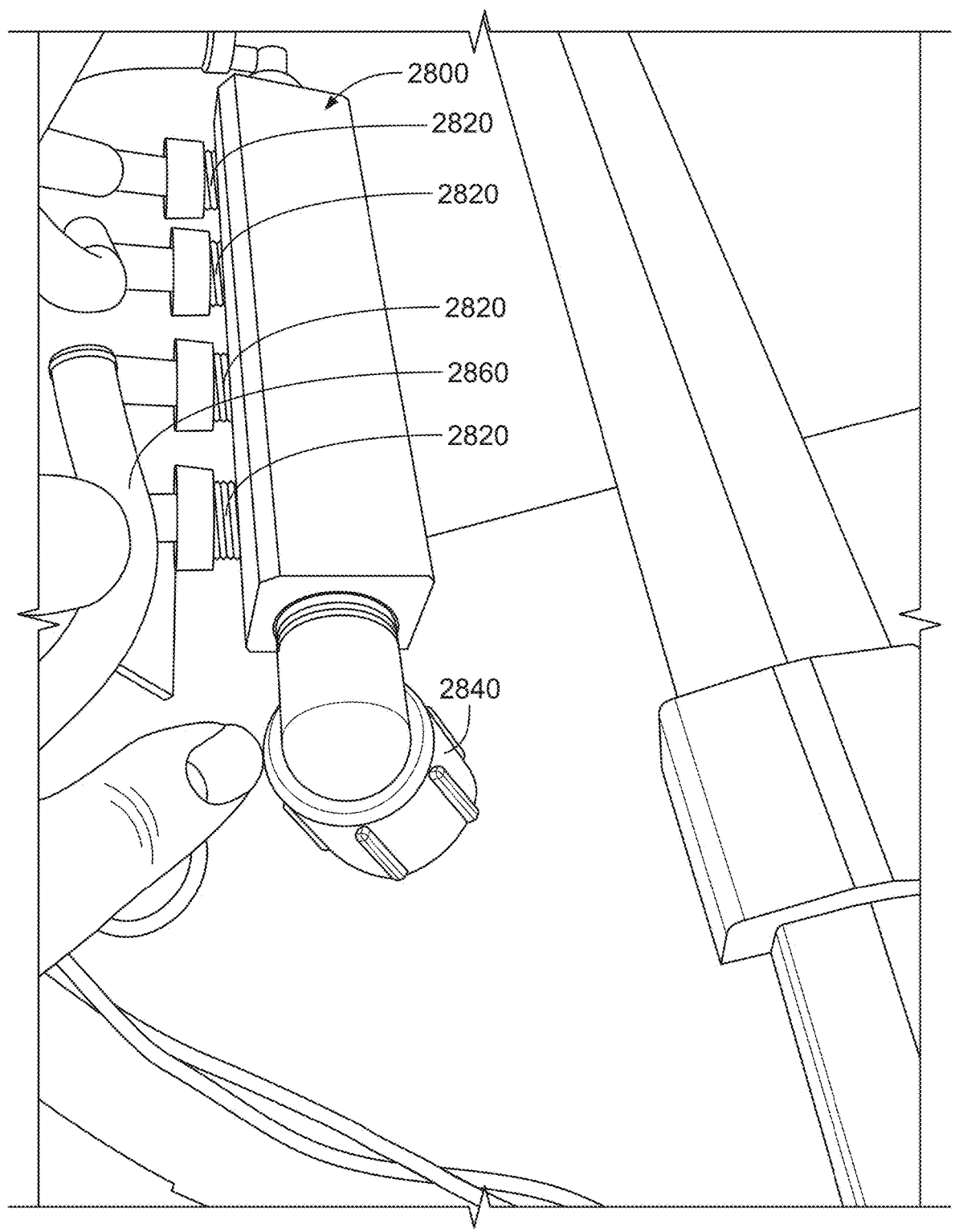
FIG. 28 illustrates an example embodiment of an outlet manifold in accordance with aspects of the innovation.

Turning now to FIG. 28, an example distribution manifold 2800 is shown. As described above, the distribution manifold 2800 can deliver temperature controlled liquid or air via a manifold outlet(s) 2820. As shown, the manifold 2800 can be effectively connected to the temperature control unit (e.g., 2700) via a threaded connector 2840. Within the temperature control unit, a hose (or other conduit) (e.g., 2650 of FIG. 26) can extend into the reservoir to draw (or otherwise accept (e.g., pressurized) liquid through the conduit (e.g., 2650). As will be understood, the temperature controlled liquid (or air) is communicated to distribution manifold 2800. The distribution manifold 2800 can include valves, connection points, outlets, and/or the like that control and/or direct flow as appropriate or desired. While the manifold 2800 has a set number of outlets (2820) it is to be understood that other aspects can have more or fewer outlets as appropriate or desired. Additionally, flow controls (e.g., valves) can be provided (not shown) so as to regulate device (e.g., collar(s), wrap(s)) performance overall.

The distribution manifold 2800 can connect to one or more distribution hoses 2860. For example, the distribution hoses 2860 can facilitate transmission of the temperature controlled liquid to one or more cervical collars such that the temperature control unit 2800 can provide temperature controlled liquid to the one or more cervical collars simultaneously as appropriate or desired. Moreover, it is to be understood that the systems (and manifold(s)) described herein can be tailored and customizable to an intended use case. For instance, if a team of 11 players are being cooled/heated on one day and on day two, only 5 players are managed, the applicable manifold(s) can be removed or swapped out thereby decreasing the number of hoses needed on day 2. Similarly, outlets on a manifold(s) can be capped (e.g., with a cap or closed valve) when not in use. These variations are to be included within this specification's scope and claims appended hereto.

While threaded connectors are illustrated, it is to be appreciated that most any connection means of attachment can be employed without departing from the spirit and/or scope of the innovation and claims appended hereto. For instance, connections can include, but are not limited to, press fit, friction fit, shark bites, or the like—all of which are to be included within the spirit and scope of the innovation and claims appended hereto.

Referring again to FIG. 28, illustrated is a close-up view of an example embodiment of a distribution manifold 2800 that is in fluid communication with the temperature control unit 2700. In the example embodiment illustrated, the distribution manifold 2800 can connect up to four external temperature controlled devices (e.g., cervical collars, wraps, etc.) via an array of connections and/or valves. In some embodiments, the distribution manifold 2800 and/or the temperature control until 2700 can selectively distribute temperature controlled liquid to individual cervical collars by switching off and on the valves of the distribution manifolds. Additionally, as described herein, the fluid can be returned to the temperature control unit, e.g., 2700, for re-processing and re-circulation.

Although not illustrated, it is to be appreciated that toggles or valves can be deployed upon the manifold or inline so as to toggle, control or restrict the flow of temperature controlled fluid throughout the system. While a specific manifold design is illustrated, it is to be understood and appreciated that most any manifold or branching mechanism can be employed without departing from the spirit and/or scope of the innovation and claims appended hereto. The manifold can be internal or external to the temperature control unit (e.g., 2700) without departing from the spirit and/or scope of the innovation. Further, in aspects, the manifold (or multiple manifolds) can be co-located or remotely located with or from the temperature control unit.

Figure 29:
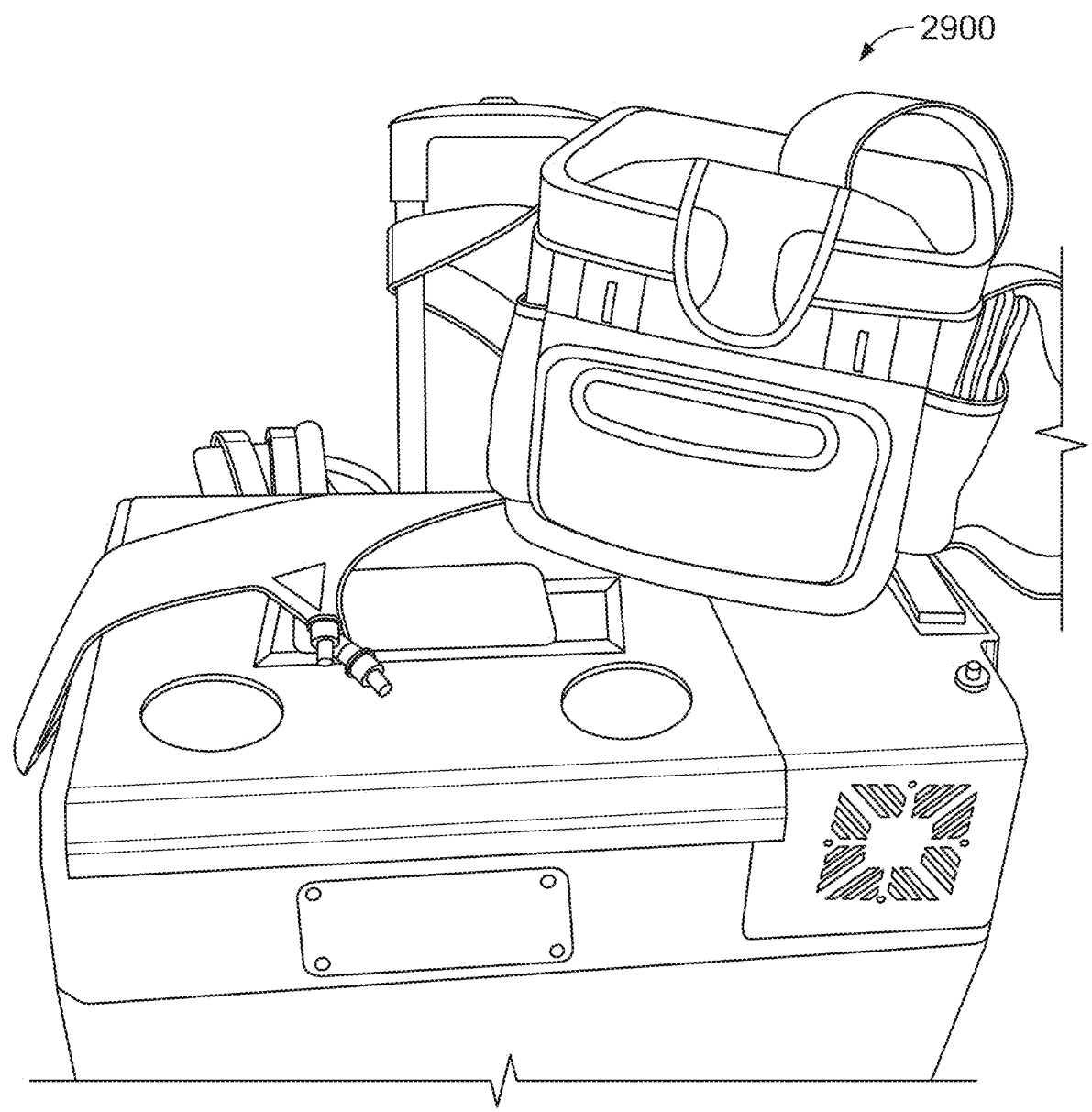
FIG. 29 illustrates an example embodiment of a cooling pump pack in accordance with aspects of the innovation.

FIG. 29 illustrates an example embodiments of a portable temperature control unit or pack 2900. As shown, the portable unit 2900 can be a soft pack or flexible walled pack that is capable of effecting temperature control of liquid (or air) as desired in accordance with a particular or desired application. The portable unit 2900 can include an outer shell manufactured of nylon, insulating fabric, plastic, other suitable material, and/or a combinations thereof. The portable unit 2900 can include a portable battery to provide power to a pump hose and/or distribution manifold. It will be appreciated that the battery can be rechargeable or disposable as desired. Similarly, the unit 2900 can be powered via an external power source as noted herein. The portable cooling pump pack can provide heating/cooling liquid to one or more cervical collars via outlet ports or valves of the distribution manifold and/or pump hose. In some aspects, the portable unit 2900 can be incorporated into a backpack or other strap-based unit for ease of use.

In other embodiments, the temperature control unit (e.g., 2600, 2700) can include insta-hot and/or insta-cool components (not shown) whereby a reservoir (e.g., 2610) need not be included. Rather, a liquid source such as a garden hose can be attached to the temperature control unit (e.g., 2600, 2700) directly. Thereafter, the insta-hot and/or insta-cold components can be employed to alter the temperature of the liquid (e.g., water) to a desired temperature for either therapeutic or medical purposes. In other embodiments, the cooling and/or heating features, functions and benefits of the innovation can be applied to a gas or air (e.g., as an air-conditioner or heat-pump). In these embodiments, rather than dispensing liquid to the devices (e.g., collar(s)), the unit can disperse temperature controlled gas or air thereby effecting the features, functions and benefits as described herein.

It will further be appreciated that, the temperature control unit (e.g., 2600, 2700, 2900) can be equipped with magnets or metal such that it is possible to mate to a collar equipped with magnets or other connection mechanism as described above. For example, a collar can have a magnet(s) (or metal tab) inserted within the material whereby it is possible to mate to another surface (e.g., for storage and convenience) such as a temperature control unit (e.g., 2600, 2700, 2900) or other surface (e.g., bench). Other mechanisms of attachment can be employed as mentioned above, including but not limited to, Velcro, grommets/hooks, adhesives or the like, without departing from the spirit and/or scope of the innovation and claims appended hereto.

Figure 30:
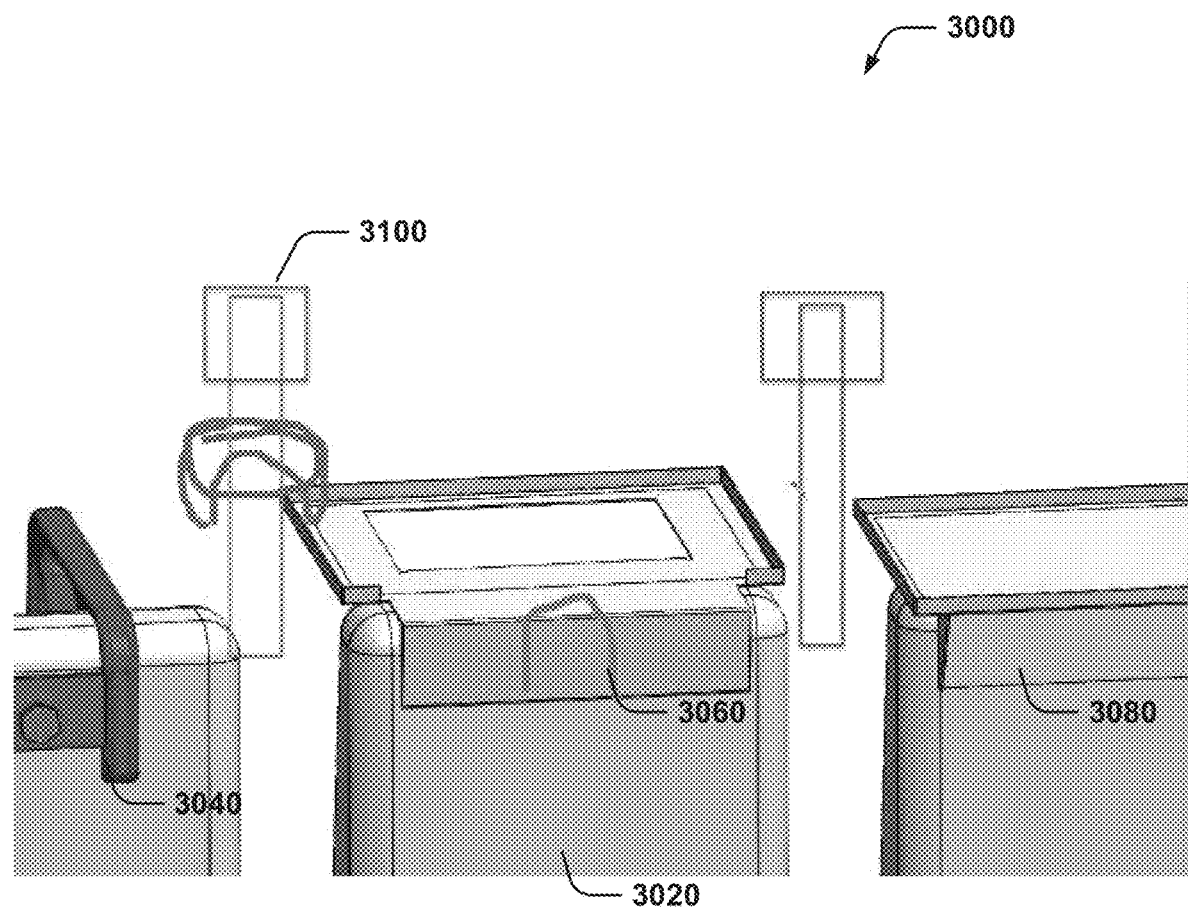
FIG. 30 illustrates example embodiments of bracketing systems in accordance with aspects of the innovation.

In yet other embodiments and referring to FIG. 30, the temperature management unit (e.g., via a cervical collar or neck wrap) can be functionally connected to (or otherwise attached or secured to) a bench, seat or other structure thereby facilitating convenience and ease of use. In other words, as illustrated in FIG. 30, a temperature control unit can be bracketed or otherwise connected to a bench or structure (e.g., 3020) by utilizing a variety of bracketing mechanisms. For example, brackets 3040, 3060 or 3080 can be employed to secure a temperature control unit to a bench, chair or other structure as desired. It will be appreciated that, having a modular and moveable attachment (bracketing) mechanism greatly enhances the convenience and usability of the system. Further, as shown in FIG. 30, the bench or structure can be equipped with a hat/helmet post or 'stove pipe' 3100 which, in embodiments can be employed to connect a therapeutic or medical device (e.g., collar(s) or wrap(s)). These embodiments will be described in greater detail below.

Figure 31:
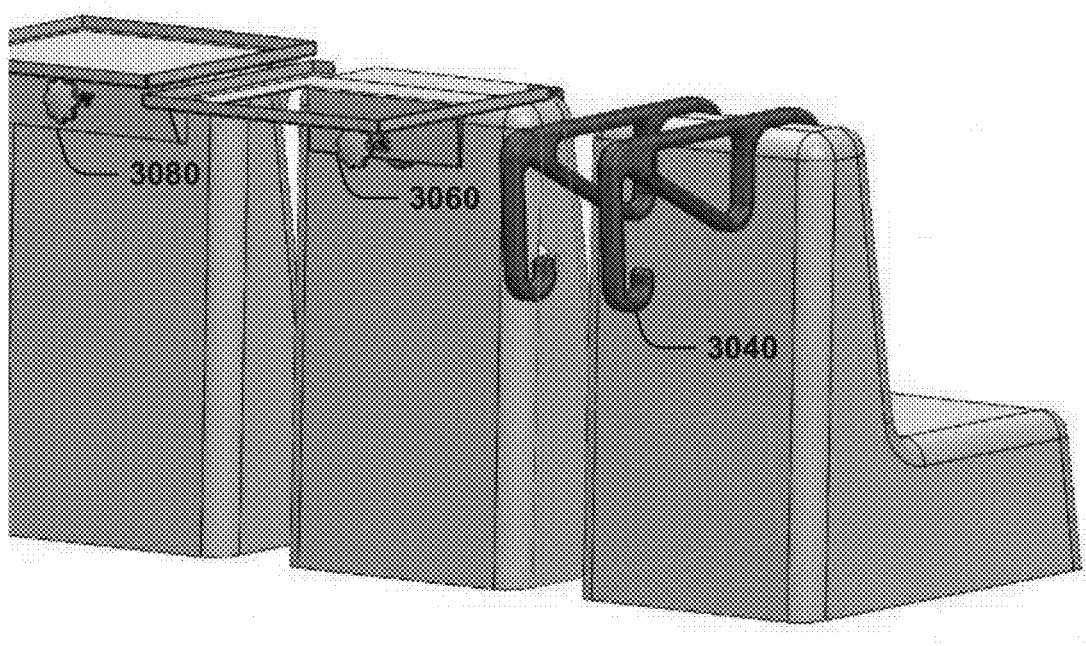
FIG. 31 illustrates an example embodiment of a bracketing system in accordance with aspects of the innovation.

FIG. 31 illustrates example brackets 3040, 3060, 3080 from the rear perspective. As shown, bracket 3040 can include hooking mechanisms that can retain a temperature control unit as well as possibly a collar, wrap, etc. Bracket 3040 can be sized (or adjustable) to securely fit over a back portion of the chair or bench. Similarly, brackets 3060 and 3080 fit over the back of the chair or bench and can be adjustable (e.g., via an adjustment wheel) to make the unit more modular as well as to securely affix to the structure.

Figure 32:
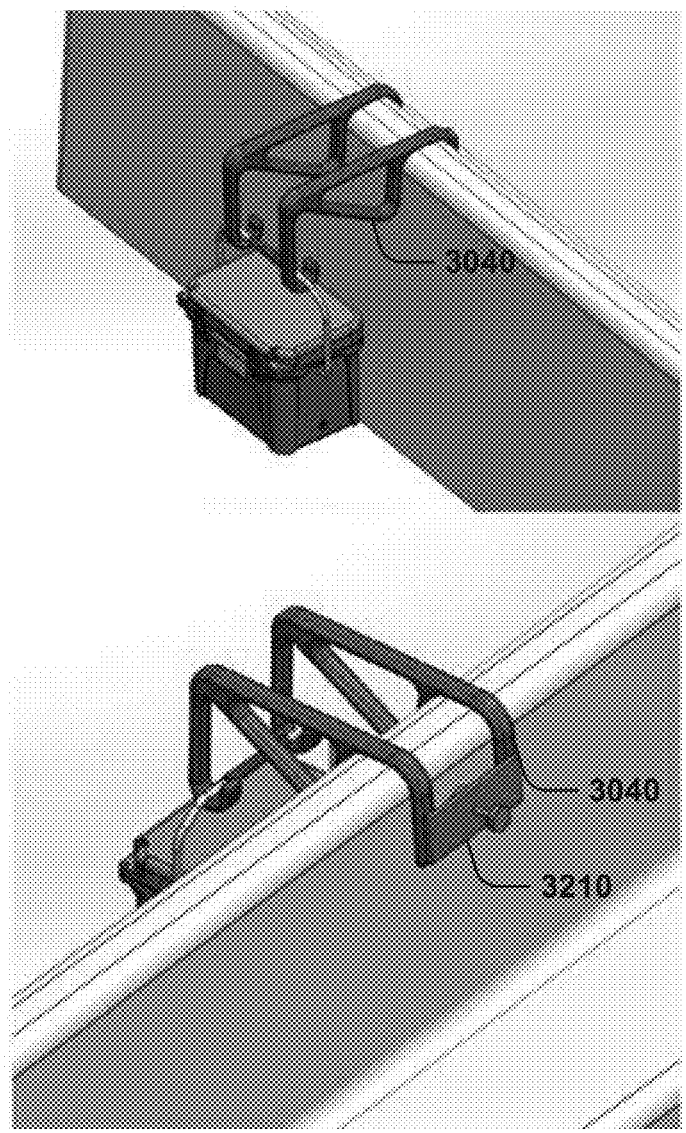
FIG. 32 illustrates example embodiments of bracketing systems in accordance with aspects of the innovation.

As described, FIGS. 30, 31 and 32 illustrate example bracketing mechanisms that can functionally (fixedly or removeably) attach a temperature control unit (e.g., heat, cool) to a bench or other stationary object. In addition to the examples of these figures, other embodiments can 'bookend' a bench or structure or otherwise attach a bracket at the base in front or rear of the bench (or structure). As illustrated in the example of FIG. 32, bracket 3040 can be employed to retain (e.g., hang) a temperature control unit, e.g., over the back of a structure such as a bench. An adjustment or retention mechanism 3210 (e.g., threaded adjustment) can be employed in aspects as shown to assist in securing the bracket 3040 to the surface.

Still other embodiments can house the temperature control unit(s) internal to the bench or structure (not shown). In yet other examples, and referring to FIG. 33, a "stove pipe" or helmet holder 3300 can be an outlet (or multiple outlets)

for temperature controlled gas (or liquid). In examples, connections can be placed over (or interconnect within) the 'stove pipe(s)' or at other convenient locations by which a hose, pipe or other conduit can be employed to transfer the temperature controlled means (e.g., liquid, air or gas) to the warming unit (e.g., collar, wrap). Here, the adapter, or conduit can be place over (or interconnected within) the 'stove pipe' thereby directing the temperature controlled medium to the collar, wrap, etc.

Figure 33:
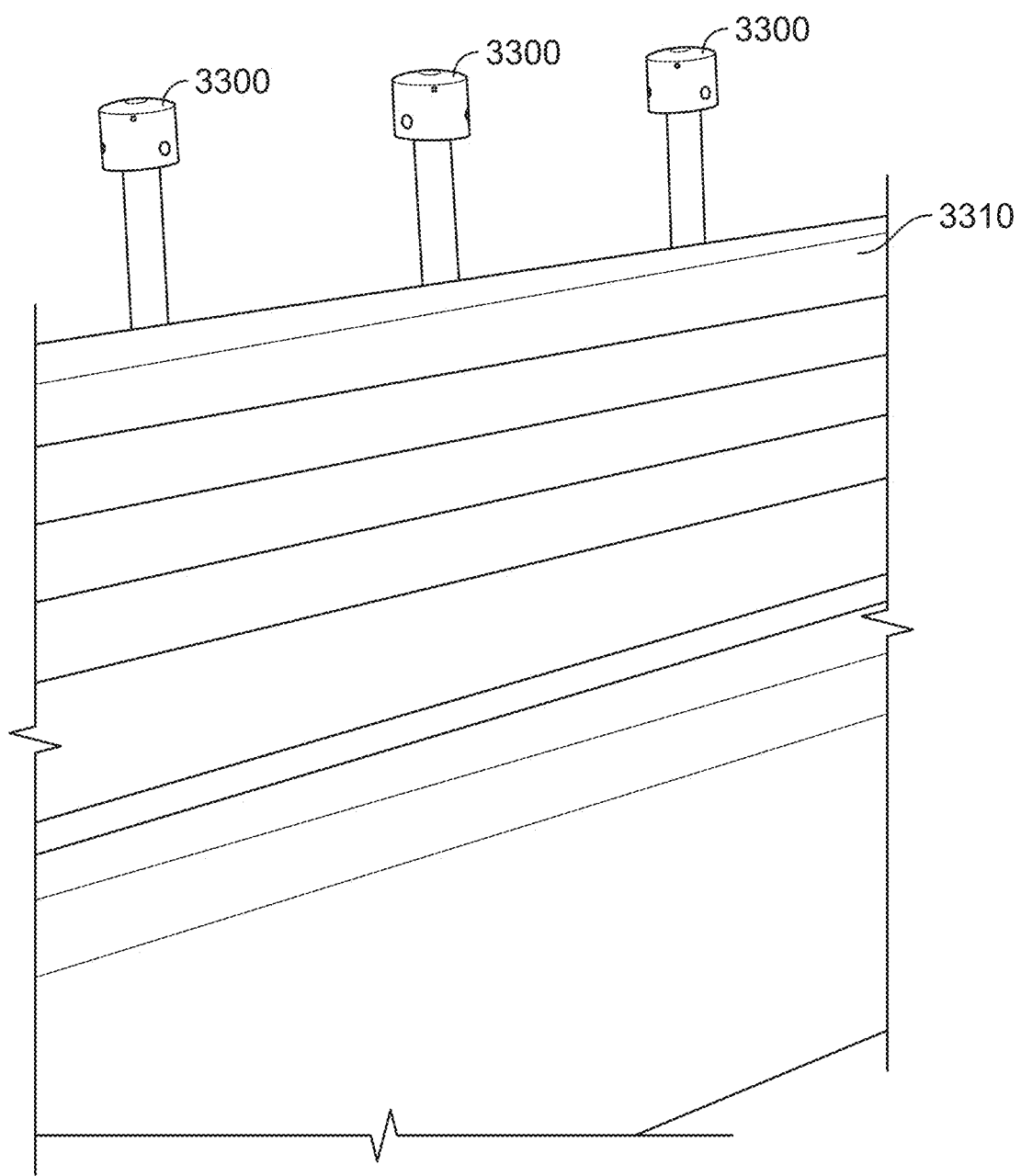
FIG. 33 illustrates an example bench or structure equipped with "stovepipes" in accordance with aspects of the innovation.

To better illustrate a bench (or stovepipe) embodiment, FIG. 33 illustrates a bench 3310 by which a bracketing system can be affixed as previously described. Here, bench 3310 can be affixed with a bracketing system (e.g., 3040, 3060 or 3080) as illustrated previously. These bracketing systems can be employed to conveniently deploy a temperature control unit.

In still other aspects, the heating/cooling functionality of the structure (e.g., bench, chair) can be employed for use within a cervical collar, neck wrap or other wrap, blanket, etc. As will be appreciated, utilization of a single temperature control source can make the unit more efficient and cost effective. Still further, in addition to, or in place of, an external temperature control unit, the innovation's features, functions and benefits described herein can be employed, for example, utilizing a hat/helmet post (or 'stovepipe') heating/cooling unit. Here, as mentioned above, an adapter or other connector (not shown) can be place over (or otherwise connected into) the existing post thereby directing/redirecting the heat/cool through a collar or wrap. As described herein, the innovation can employ most any liquid or gas, including air, to effect temperature management.

Figure 34:
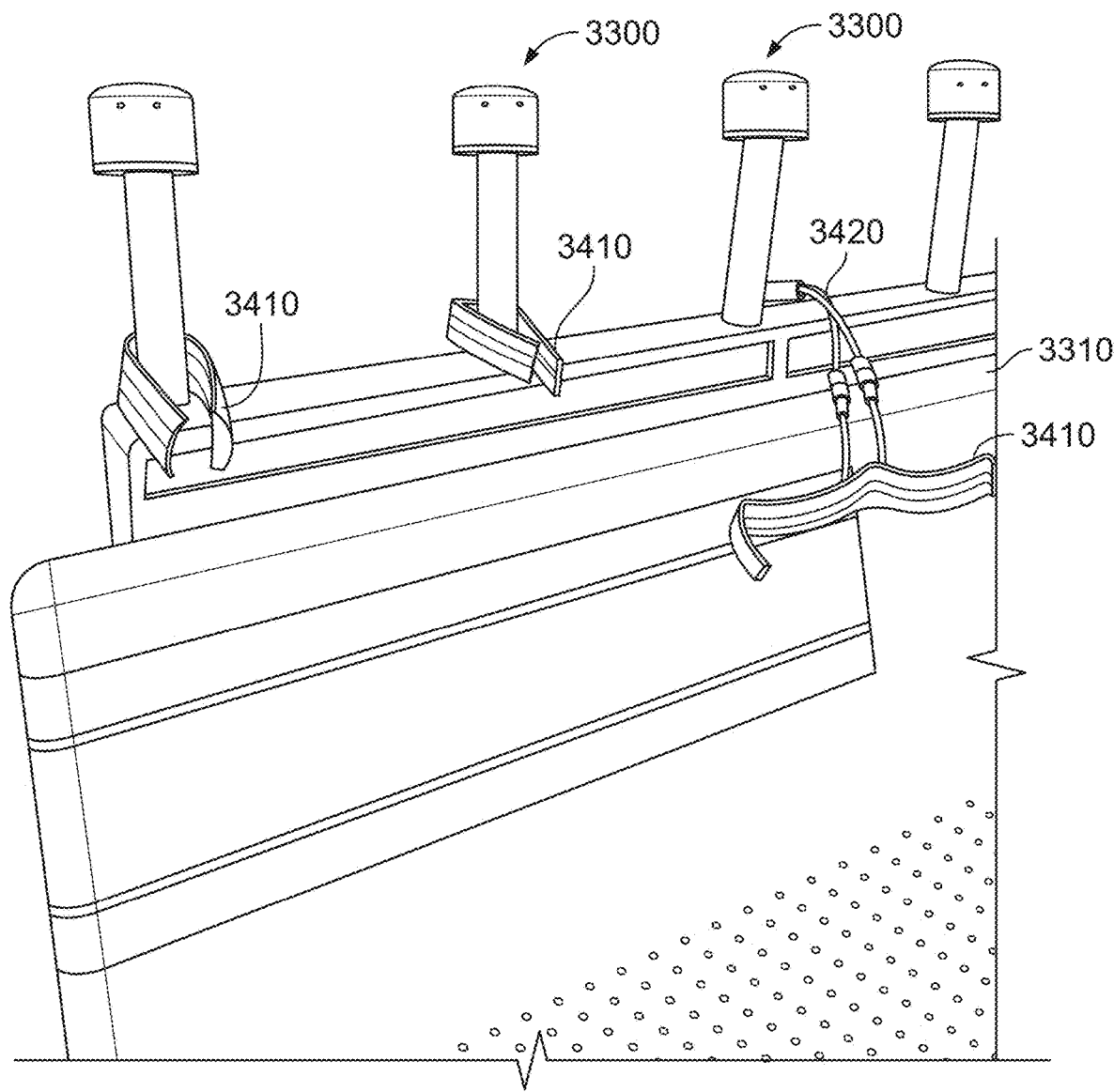
FIG. 34 illustrates an example bench or structure equipped with "stovepipes" in accordance with aspects of the innovation.
Figure 35:
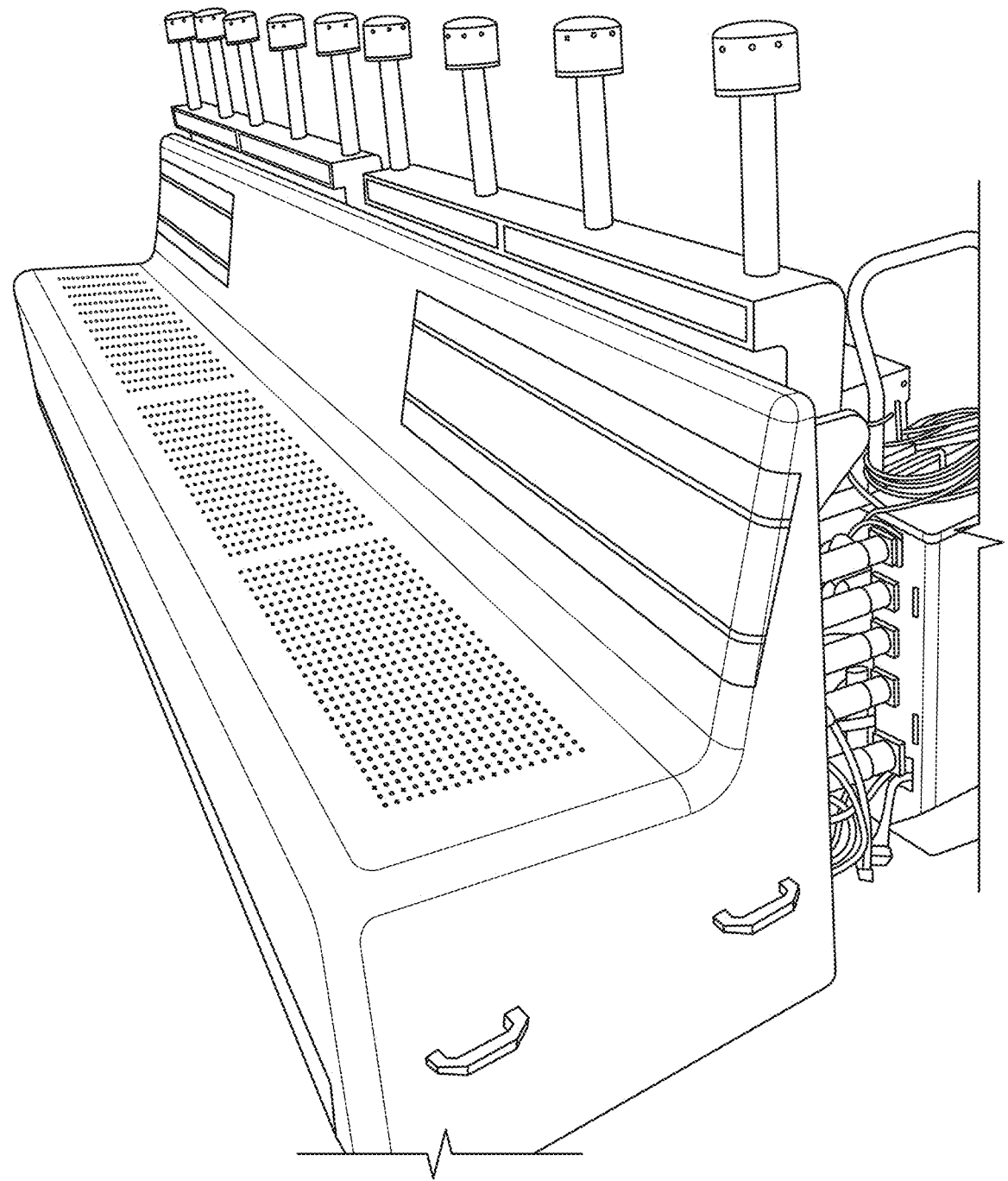
FIG. 35 illustrates an example bench or structure equipped with "stovepipes" in accordance with aspects of the innovation.
Figure 36:
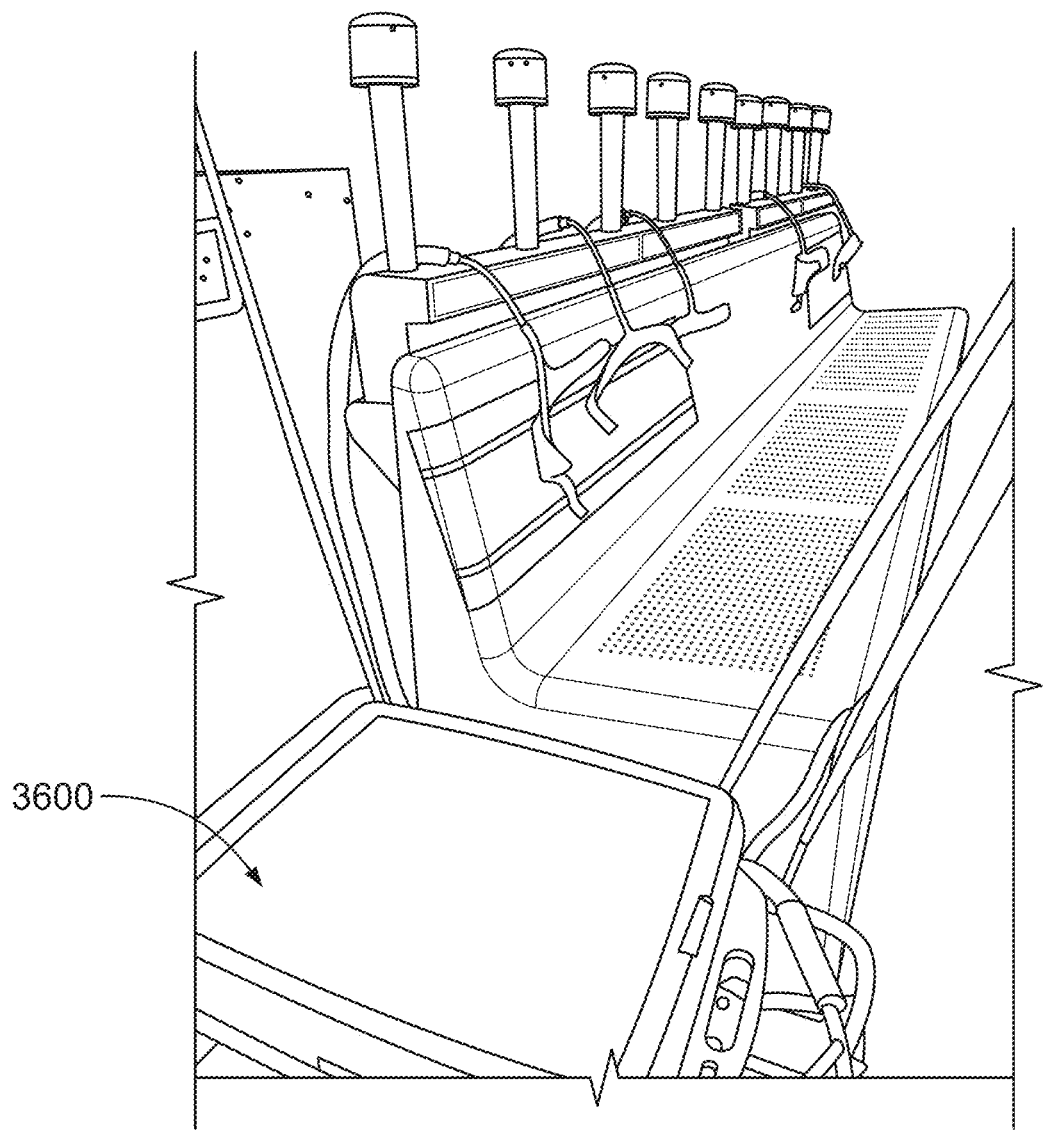
FIG. 36 illustrates an example bench or structure equipped with "stovepipes" in accordance with aspects of the innovation.

Referring now to FIGS. 34-37, embodiments that incorporate the features, functions and benefits into a bench are illustrated. Here, as shown in FIG. 34, a neck wrap 3402 can be functionally interconnected to the bench 3310 having stovepipes (e.g., coolers/warmers) 3300. In this example, the stovepipes may be used as an outlet for the conduit 3420 which transfers the gas/liquid to the wrap 3410. In other aspects, the stovepipes 3300 are merely used to retain or hang the wraps for ease of use. FIG. 35 illustrates a conventional temperature controlled bench that can be equipped with the temperature controlled features, functions and benefits of the innovation (as shown in FIG. 36). As shown in FIG. 36, the wraps can be individually connected to the temperature control unit (e.g., 3600). Alternatively, and as described above, the temperature control unit 3600 can be plumbed or interconnected into the bench whereas the conduit and wraps can be connected to outlets from the bench or alternatively, the stovepipes.

Figure 37:
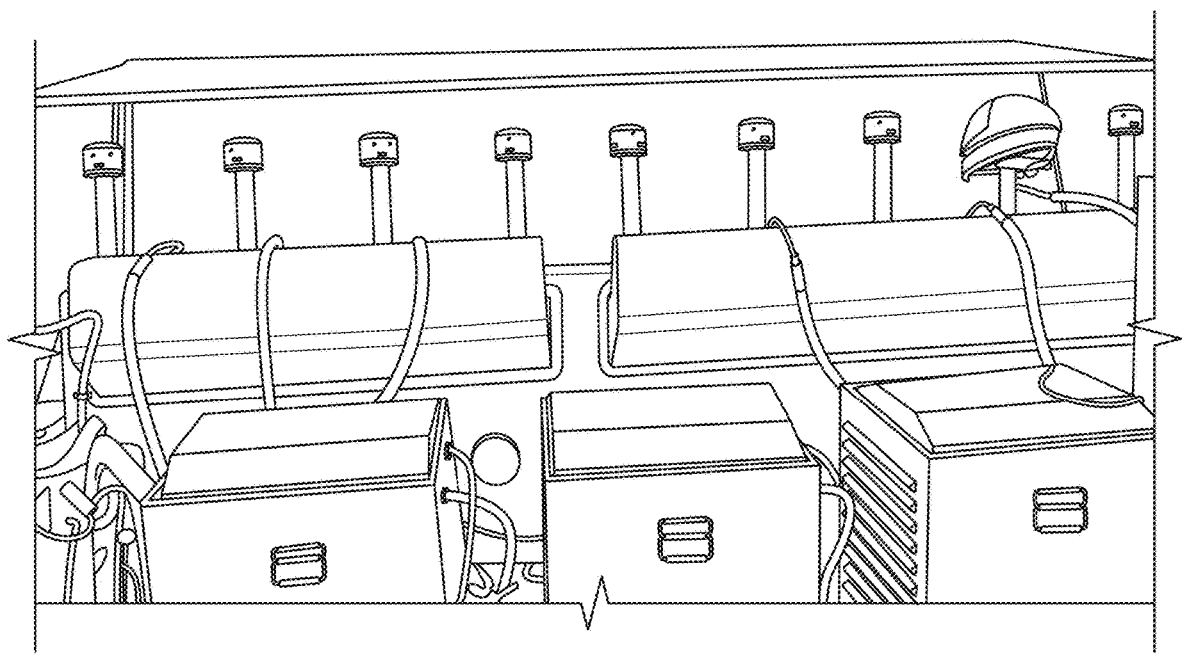
FIG. 37 illustrates an example bench or structure equipped with "stovepipes" in accordance with aspects of the innovation.

FIG. 37 illustrates the embodiment of FIG. 36 from the rearward perspective. As will be appreciated, temperature control units can be employed to enable multiple wraps without departing from the spirit and/or scope of the innovation and claims appended hereto.

Figure 38:
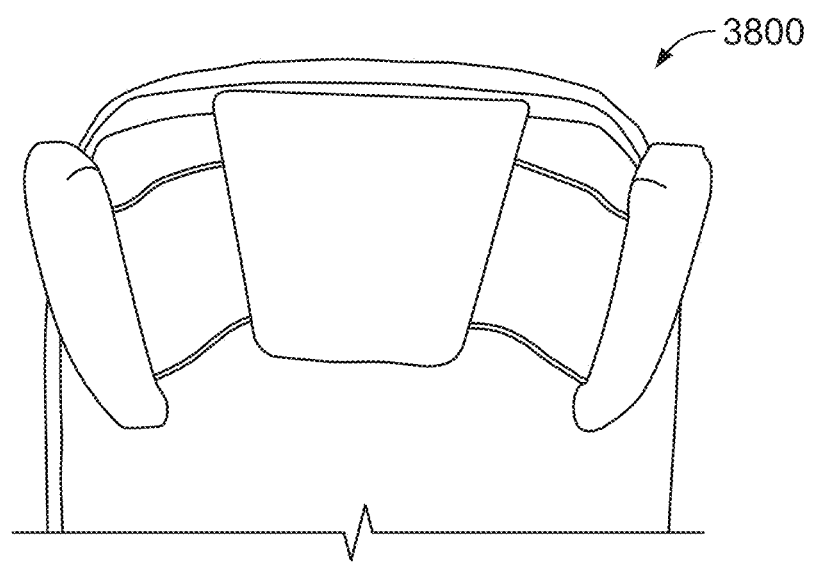
FIG. 38 illustrates an example adjustable head or neck wrap in accordance with aspects of the innovation.
Figure 39:
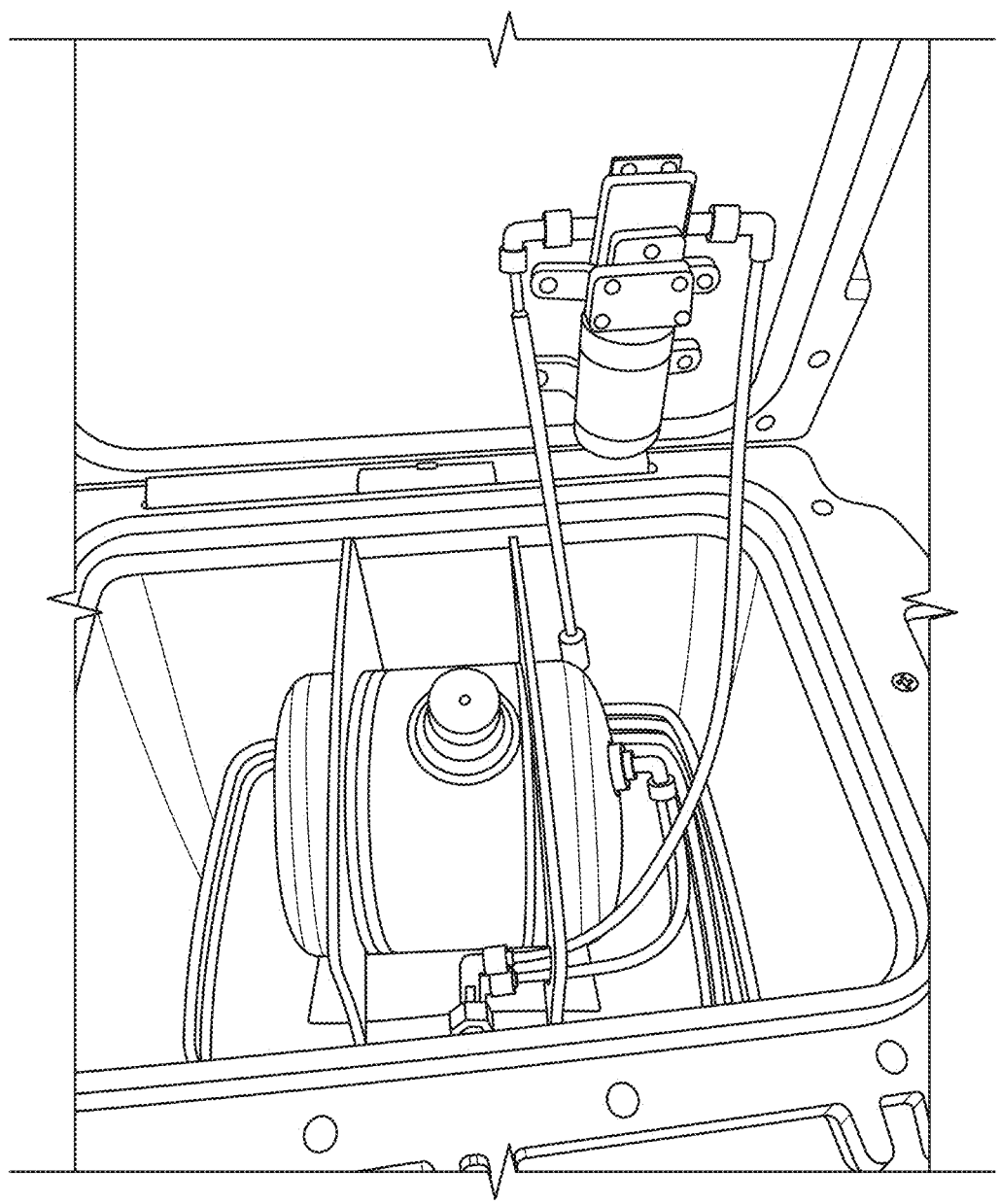
FIG. 39 illustrates an example interior of a temperature control device in accordance with aspects of the innovation.
Figure 40:
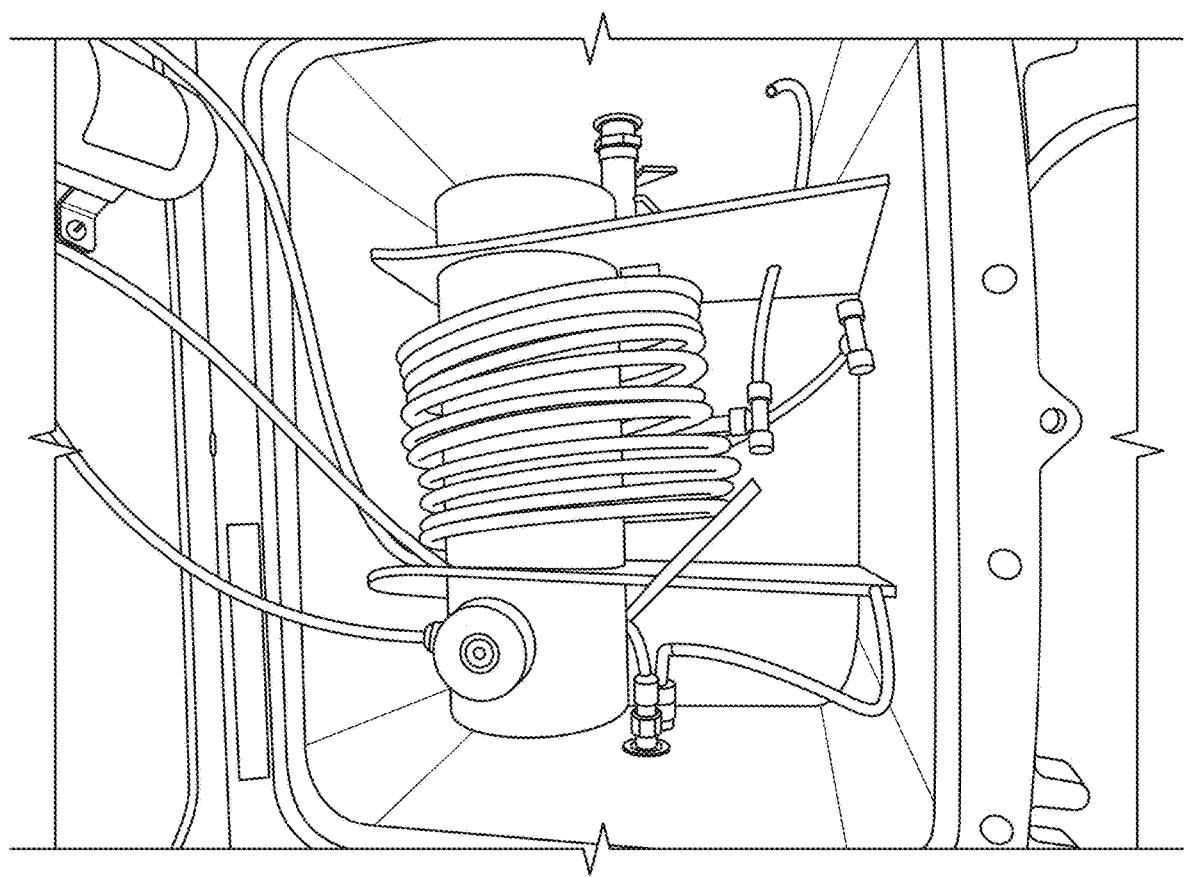
FIG. 40 illustrates an example interior of a temperature control device in accordance with aspects of the innovation.
Figure 41:
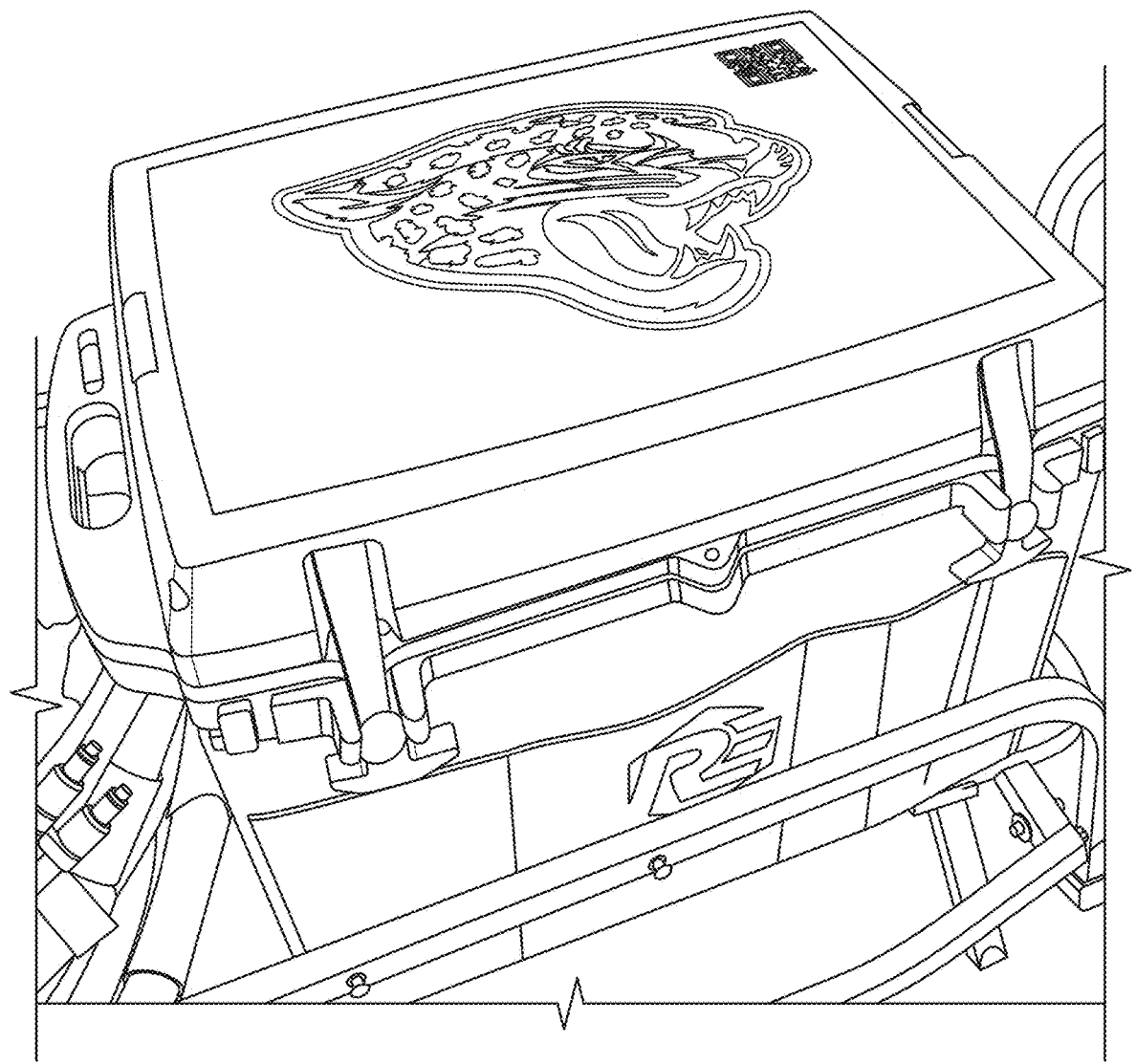
FIG. 41 illustrates an example temperature control device in accordance with aspects of the innovation.
Figure 42:
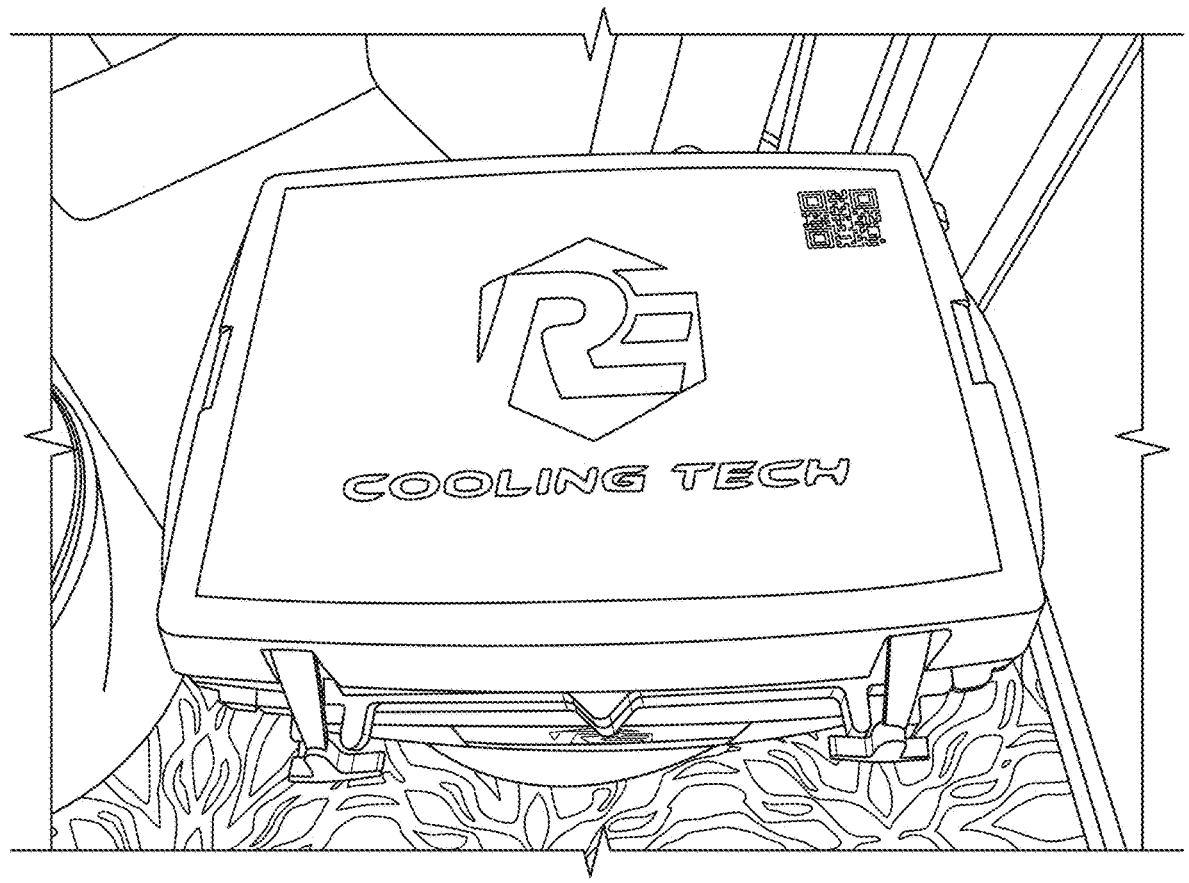
FIG. 42 illustrates an example temperature control device in accordance with aspects of the innovation.

In still other embodiments, the features, functions and benefits of the innovation can be employed by way of a preset or pre-disposed neck (or head) wrap 3800 as shown in FIG. 38. Here, as is to be appreciated, the temperature control unit can be adjustable both in height as well as to "form fit" around a user (e.g., athlete). By way of visual illustration/description and further description and without limitation, here, the unit can be akin to a headrest in an airplane or automobile whereby the rest is adjustable around a user/passenger's head or neck region. Similarly, other body wraps are contemplated that can encompass, for example, lumbar regions, legs, feet or the like.

In the aspect of a neck wrap, the wrap can be configured (e.g., size, orientation, etc.) to be able to be easily configured around a user's (e.g., athlete's) neck region. Additionally, as discussed above, the unit can be adjustable for height as well as forward/rearward so as to be configurable and usable for a variety of individuals having different, heights, sizes and shapes. In addition to the neck region, it is to be understood that the unit can also be used upon a user's head region to manage temperature and/or provide therapeutic effect. The temperature management can include any of the aspects described herein, e.g., internal to the structure (e.g., bench, chair), external (e.g., heat pump), via helmet post or "stove pipe," etc. Additionally, the wrap 3800 can be mounted upon a post (e.g., stovepipe) or other suitable structure so as to enable effective and adaptable adjustment. These examples are for illustrative purposed and not intended to limit the scope of the innovation described (and claimed) herein.

As noted above, the innovation disclosed herein is not limited to a cervical collar to medically treat the neck area of a person. The innovation can be applied to any portion of the body that requires therapeutic temperature management. Thus, while a particular type of cooling device is described and illustrated, it is to be understood that alternative aspects can employ the cooling device without departing from the spirit and/or scope of the innovation. It is further to be appreciated that the spirit and scope of the innovation can be accomplished using equipment of differing size, location, etc. For instance, while example larger (or mid-sized) temperature control units are shown in FIGS. 39-42, other units can be employed to effect temperature management—for example, units with much smaller (or larger) footprint(s). In one example, the unit can be akin to the size of a standard "insulin pump" without departing from the spirit and/or scope of the innovation and claims appended hereto. The example images of FIGS. 39-42 are provided to exhibit enablement and not limitation of examples of the innovations feature or functions.

In yet other aspects, the temperature control systems described herein can be communicatively (e.g., wired or wirelessly (e.g., Bluetooth, WiFi, etc.)) connected to a remote management device (e.g., smartphone, laptop, tablet, computer, etc.) that is capable of management of the functionality of the innovation as described herein. For instance, remote management, can include, but, is not limited to, on/off capability, temperature management, distribution valve control, timer set/reset, or the like. It is further to be appreciated that, via a distribution manifold, devices (e.g., wraps) can be set to differing temperature, for example, by regulating valves or temperature controls of the system.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A temperature control pump system, comprising:
   a reservoir that holds a liquid,
   control that regulates temperature of the liquid within the reservoir;
   a pump hose that transfers the liquid from the reservoir;
   a distribution manifold attached to the pump hose to receive the liquid and distribute the liquid to at least two temperature controlled wraps, wherein the distribution manifold attaches to the at least two temperature controlled wraps via at least two outlet ports.

2. The system of claim 1, wherein the control, pump, or distribution manifold is powered via a battery pack.

3. The system of claim 2, wherein the reservoir comprises insulating material.

4. The system of claim 2, wherein the temperature control pump system is a portable backpack comprising insulating material.

5. A temperature control system, comprising:
   a temperature control unit that selectively outputs a substance at or near a desired temperature;
   a distribution manifold that receives the substance and routes a portion of the substance to a plurality of therapeutic or medical devices.

6. The temperature control system of claim 5, wherein the plurality of therapeutic or medical devices comprise, neck wraps or head wraps or combinations thereof.

7. The temperature control system of claim 5, wherein the temperature control unit is interconnected to at least one "stovepipe".

8. The temperature control system of claim 5, wherein the distribution manifold includes pressure regulating valves.

9. The temperature control system of claim 5, wherein each outlet of the distribution manifolds includes an on/off regulator or switch.

10. The temperature control system of claim 9, further comprising a control element that is communicatively coupled to a remote management device, wherein the remote management device can selectively regulate temperature or output of the substance.

11. The temperature control system of claim 10, wherein the control element is communicatively coupled wirelessly.

12. The temperature control system of claim 5, wherein the therapeutic or medical device is a form fitting unit having at least two adjust mechanisms that conform to a user's neck region.

13. The temperature control system of claim 5, further comprising a bracketing system that facilitates attachment of the temperature control unit to a surface of a bench.

* * * * *